(12) United States Patent
McMaster et al.

(10) Patent No.: US 7,968,327 B2
(45) Date of Patent: Jun. 28, 2011

(54) NUCLEIC ACID QUANTITATION FROM TISSUE SLIDES

(76) Inventors: Gary McMaster, Ann Arbor, MI (US); Joan Davies, Los Gatos, CA (US); Yunqing Ma, Cupertino, CA (US); Yuling Luo, San Ramon, CA (US)

( * ) Notice: Subject to any disclaimer, the term of this patent is extended or adjusted under 35 U.S.C. 154(b) by 0 days.

(21) Appl. No.: 11/893,356

(22) Filed: Aug. 14, 2007

(65) Prior Publication Data
US 2008/0050746 A1  Feb. 28, 2008

Related U.S. Application Data

(60) Provisional application No. 60/838,578, filed on Aug. 17, 2006.

(51) Int. Cl.
  C12Q 1/68 (2006.01)
  C12P 19/34 (2006.01)
  C12N 1/08 (2006.01)
  G01N 33/00 (2006.01)
  C07H 21/04 (2006.01)

(52) U.S. Cl. .......... 435/270; 435/6; 435/91.2; 435/219; 436/94; 536/23.1

(58) Field of Classification Search .......... None
See application file for complete search history.

(56) References Cited

U.S. PATENT DOCUMENTS

| | | | |
|---|---|---|---|
| 4,868,105 A | 9/1989 | Urdea et al. | |
| 5,093,232 A | 3/1992 | Urdea et al. | |
| 5,124,246 A | 6/1992 | Urdea et al. | |
| 5,594,118 A | 1/1997 | Urdea et al. | |
| 5,635,352 A | 6/1997 | Urdea et al. | |
| 5,710,264 A | 1/1998 | Urdea et al. | |
| 5,780,227 A | 7/1998 | Sheridan et al. | |
| 5,814,448 A * | 9/1998 | Silverstein et al. | 435/6 |
| 5,849,481 A | 12/1998 | Urdea et al. | |
| 6,489,105 B1 | 12/2002 | Matlashewski et al. | |
| 6,677,157 B1 | 1/2004 | Cohen | |
| 2002/0172950 A1 | 11/2002 | Kenny et al. | |

OTHER PUBLICATIONS

Roche Applied Science, "High Pure RNA Parafin Kit" (package insert) Jul. 2005.*
Bibikova et al., "Quantitative Gene Expression Profiling in Formalin-Fixed, Paraffin-Embedded Tissues Using Universal Bead Arrays," American Journal of Pathology, vol. 165, No. 5, Nov. 2004, pp. 1799-1807.*
Bibikova et al. (2004) "Quantitative gene expression profiling in formalin-fixed, paraffin-embedded tissues using universal bead arrays," *Am J Pathol*, 165(5):1799-1807.
Bustin (2002) "Quantification of mRNA using real-time reverse transcription PCR (RT-PCR): trends and problems," *J Mol Endocrinol*, 29:23-39.

(Continued)

*Primary Examiner* — Bradley L Sisson
(74) *Attorney, Agent, or Firm* — Quine Intellectual Property Law Group, P.C.; Gary Baker

(57) ABSTRACT

This invention provides methods of quantitating nucleic acids from problematic samples, such as aged samples, formalin fixed samples, paraffin embedded samples, samples with aneuploid cells, and cells with fragmented nucleic acids. Methods include techniques to efficiently solublize the nucleic acids under non-denaturing conditions from preserved clinical samples without resort to organic extractions, to normalize cell counts regardless of aneuploidy, to access the fragmentation state of the nucleic acids, and to provide standard curves for degraded nucleic acid samples.

20 Claims, 24 Drawing Sheets

OTHER PUBLICATIONS

Bustin and Nolan (2004) "Pitfalls of quantitative real-time reverse-transcription polymerase chain reaction," *J Biomol Tech*, 15(3):155-166.

Cronin (2004) "Measurement of gene expression in archival paraffin-embedded tissues: development and performance of a 92-gene reverse transcriptase-polymerase chain reaction assay," *Am J Pathol*, 164(1):35-42.

Lehmann and Kreipe (2001) "Real-time PCR analysis of DNA and RNA extracted from formalin-fixed and paraffin-embedded biopsies," *Methods*, 25(4):409-418.

Masuda et al. (1999) "Analysis of chemical modification of RNA from formalin-fixed samples and optimization of molecular biology applications for such samples," *Nucleic Acids Res,*, 27(22):4436-4443.

Wilber and Urdea (1998) "Quantification of HCV RNA in clinical specimens by branched DNA (bDNA) technology," *Methods in Molecular Medicine: Hepatitis C*, 19:71-78.

Yang et al. (2006) "Direct quantification of gene expression in homogenates of formalin-fixed, paraffin-embedded tissues, " *Biotechniques*, 40(4):481-486.

* cited by examiner

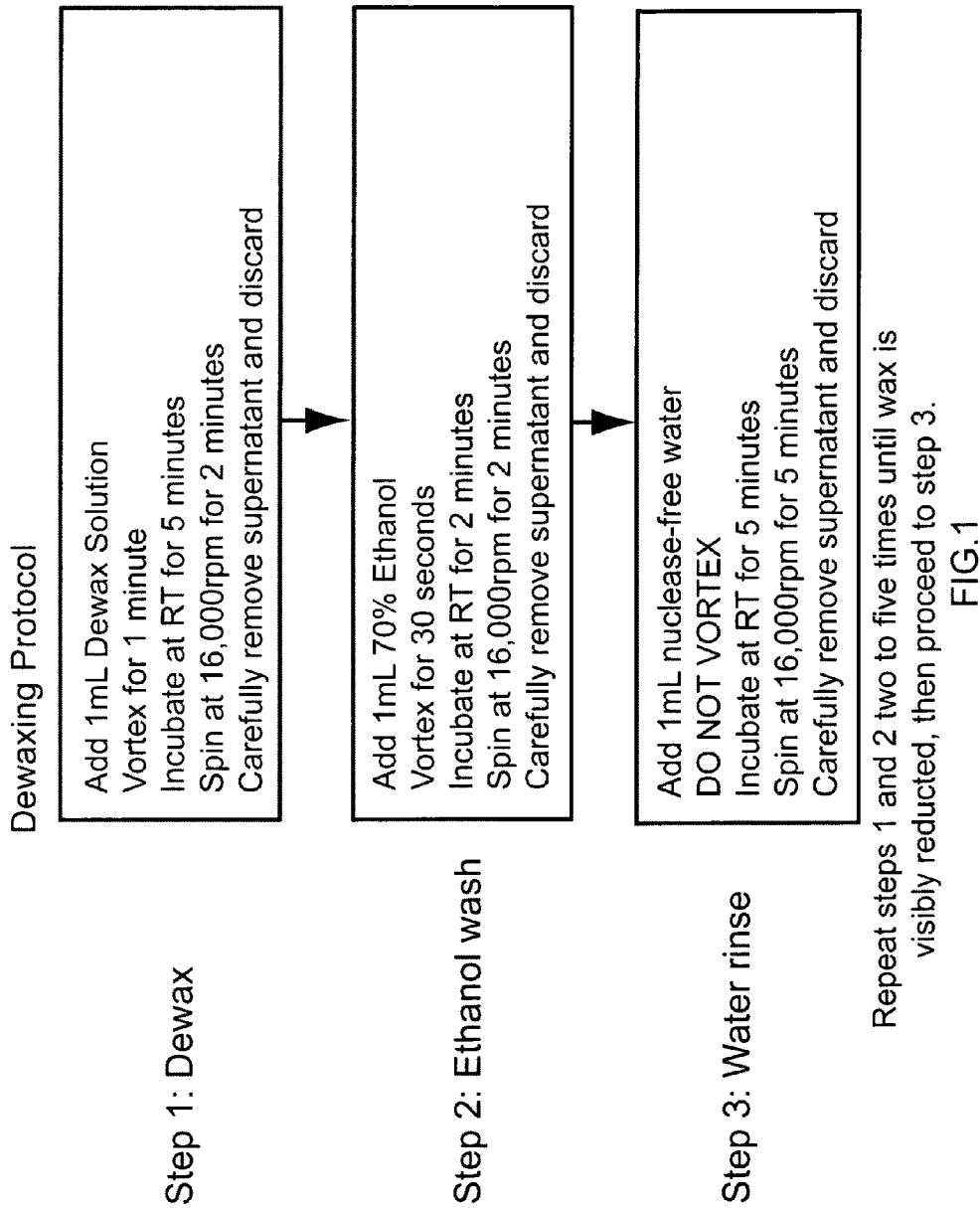

Alternative Sample Handling Procedure

- Add 300 μl Aqueous Solution supplemented with Proteinase K (0.3 mg/ml) per 60-100 microns (25-250mm$^2$) pooled tissue sections or 10mg unsectioned tissue.

- Paraffin separates from the tissue lysate during overnight Proteinase K digestion at 65°C and, if abundant, forms a visible layer above lysate.

- Liquid paraffin can be removed with a pipettor or allowed to solidify at RT during centrifugation, pierced, and the lysate removed from underneath.

- Transfer supernatant to a fresh microfuge tube.

- Use immediately or store at -80°C for future use.

FIG. 2

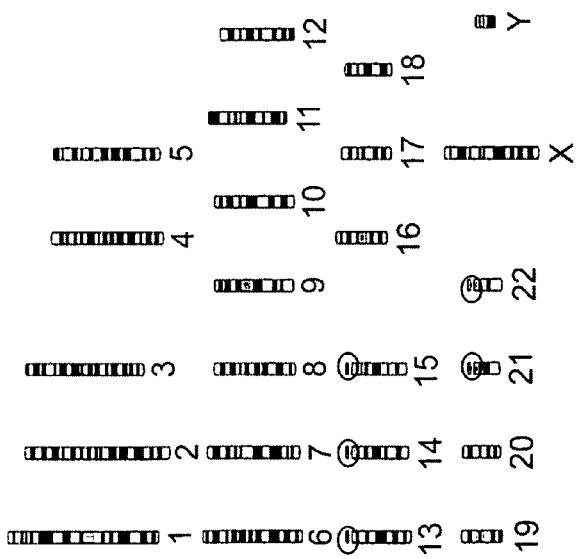
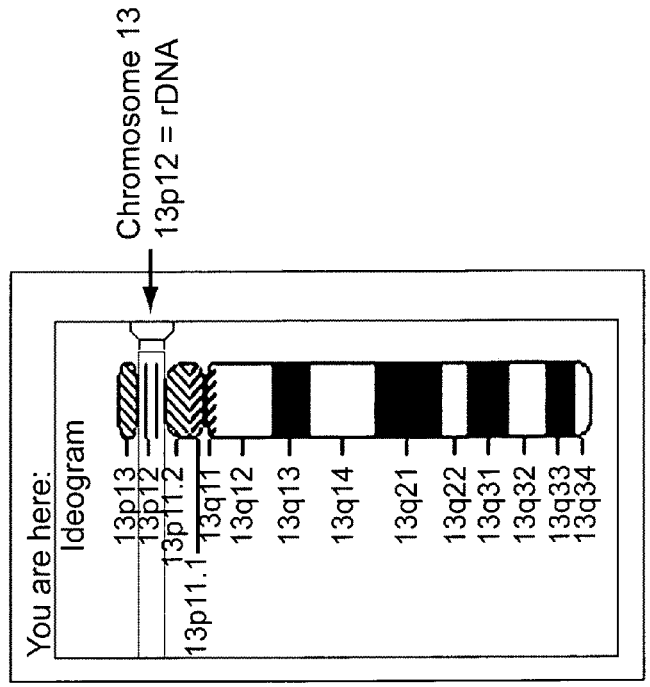
FIG. 4A

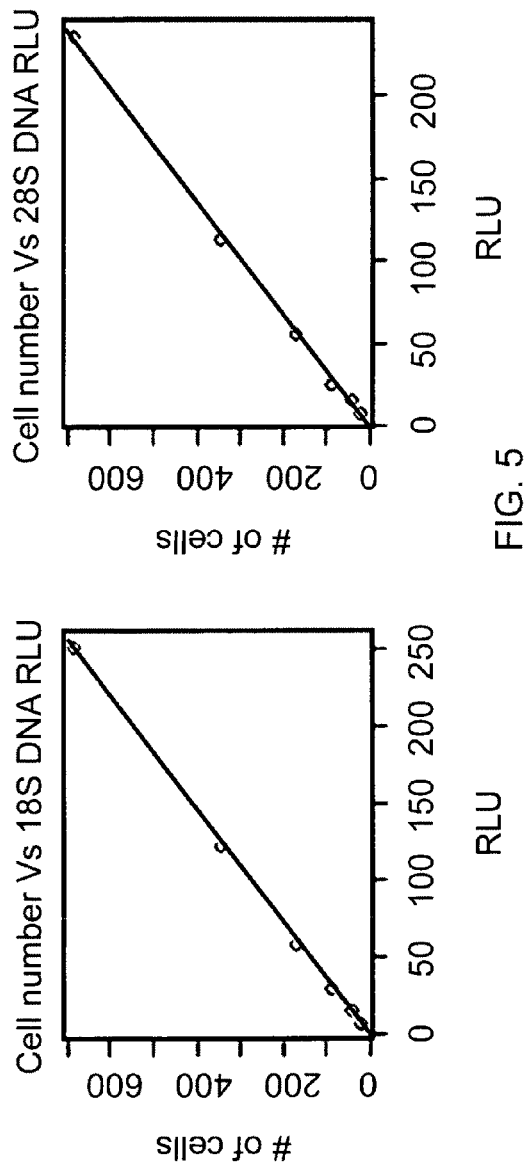

FIG. 5

Cell Number Standard Curve

● A major difficulty in studying differential gene expression is how to normalize for heterogeneity between samples. Ideally, the gene transcript number (mRNA copy) is corrected for the number of cells analyzed. This is not practical for FFPE tissue sections.

● Ribosomal DNA (18S rDNA, 28S rDNA) is used to normalize for cell number by directly counting cells and measuring the amount of ribosomal DNAs measuring an average of 4000 cells pooled from 10 different cell lines.

NUCLEIC ACID QUANTITATION FROM TISSUE SLIDES

CROSS-REFERENCE TO RELATED APPLICATIONS

This application claims priority to and benefit of a prior U.S. Provisional Application No. 60/838,578, Nucleic Acid Quantitation from Tissue Slides, by Gary McMaster, et al., filed Aug. 17, 2006. The full disclosure of the prior application is incorporated herein by reference.

FIELD OF THE INVENTION

The present invention is in the field of nucleic acid extraction and quantitation from cells and tissues. Nucleic acids are extracted from embedded clinical samples without the use of hydrophobic solvents. Ribosomal DNA references and/or degraded in vitro RNAs are used to normalize standard curves and to establish nucleic acid copy numbers per cell.

BACKGROUND OF THE INVENTION

Formalin-fixed, paraffin-embedded (FFPE) tissue offers a vast source of biopsy specimens for which the clinical outcome is well documented and thus an optimal resource for retrospective studies (Lewis, F. et al. 2001; Yang et al. 2006). Access to and use of human specimens is an essential part of the cancer research and drug discovery infrastructure, enabling researchers to identify drug targets, develop lead compounds and understand drug metabolism. Research using human specimens can help predict drug response and toxicity, as well as short and long term clinical outcome. New technologies and information gained from mapping the human genome continue to fuel a growing need for researchers in academia and industry, for-profit and not-for-profit, to have access to good quality human specimens to expedite cancer drug discovery. Many different types of human specimens are required to support these studies: normal and malignant tissues, blood, other fluids, and the proteins, DNA and RNA that can be extracted from them.

Because all surgical procedures performed in the U.S. must obtain tissue samples for pathology diagnosis, primary sources for human specimens are hospital operating rooms and pathology laboratories. More than 160 million pathology specimens (most of them fixed tissue in wax blocks) are currently stored in the United States (Eiseman and Haga, 1999).

Tissue blocks are routinely fixed and embedded in paraffin, then sectioned with a microtome, and the sections affixed to microscope slides. The paraffin-embedded tissue sections have required dewaxing prior to analysis of nucleic acids to allow penetration by aqueous solutions.

For example, using a clean razor blade, FFPE sections have been scraped off slides and transferred into microfuge tubes for processing. The traditional method of paraffin removal involves organic extractions using xylene and graded alcohols. This procedure is time-consuming, cumbersome, and requires special handling, as xylene is a highly toxic chemical that emits noxious fumes. After 10 sections (60-100 microns/ 25-250 mm$^2$) of FFPE specimens from the same tissue block are scraped off from glass slides into the tubes using a scalpel, one milliliter of hydrophobic solvent is added, e.g., xylene-containing EZDeWax™ (BioGenex, San Ramon, Calif., USA); see FIG. 1. After vortex mixing and incubating at room temperature for 5 min, the tissue samples are centrifuged in a microcentrifuge at 16,000×g for 2 min, and the supernatants removed. One milliliter 70% ethanol can be added to the samples, and the samples vortex mixed and centrifuged in a microcentrifuge at 16,000×g for 2 min. The sample wax is then extracted repeatedly into the xylene phase and the residue washed with 70% ethanol for two-five more times before continuing to the next step of tissue homogenate preparation or total RNA isolation (Yang et al., 2006).

The phase extraction dewaxing protocols are time consuming and laborious. The repeated handling, aspirations and tube transfers can result in non-quantitative harvests of the nucleic acids. The repeated vortexing and exposure to harsh solvents can cause sample degradation.

Additional problems exist in the quantitation of nucleic acids from preserved clinical specimens. For example, RNA quality can be affected by sample collection, formalin fixation and tissue processing. This can compromise, e.g., the ability to measure RNA in FFPE tissue blocks. The nucleic acids ultimately extracted from embedded clinical samples are often highly degraded and fragmented. Qualitative and quantitative assay errors often result when these extracts are evaluated by standard analytical techniques. What's more, incomplete extractions can introduce error into calculations, such as mRNA copy number determinations. One problem in measuring RNA from FFPE tissue blocks can be fragmentation of the RNA fragments, cross-linking, and base modifications induced by formalin-fixation procedures. Two processes that reduce the length of RNA molecules in formalin-fixed tissues are degradation and fragmentation (hydrolysis). RNA degradation can occur through enzymatic cleavage before the tissue encounters a fixative and is thus subject to the collection procedure of the samples. Fragmentation of RNA molecules can be caused by the formalin fixative and therefore varies substantially depending on formalin conditions employed (Lehmann U, Kreipe H: Real-time PCR analysis of DNA and RNA extracted from formalin-fixed and paraffin-embedded biopsies, Methods 2001, 25:409-418). The exact causes for the fragmentation are not known, and thus it has been unclear how to solve this problem.

The current state-of-the-art technology for measuring RNA is quantitative PCR (QPCR). However, several recent reports comparing RNA quantification in frozen and FFPE tissues demonstrate that only 3-5% of RNA transcripts are available for detection by QPCR after formalin fixation (Bibikova M, Talantov D, Chudin E, Yeakley J M, Chen J, Doucet D, Wickham E, Atkins D, Barker D, Chee M, Wang Y, Fan J B: Quantitative gene expression profiling in formalin-fixed, paraffin-embedded tissues using universal bead arrays, Am J Pathol 2004, 165:1799-1807). This problem is independent of whether the reverse transcription step uses oligo-dT or random priming. A viable explanation for this problem is that reverse transcription and/or QPCR are severely affected by formalin mediated mono-methylolation of bases in RNA. Attempting to compensate for this problem, the expression of genes of interest has been normalized to internal housekeeping genes. However, this is often inadequate because adenines are more susceptible to alteration by formalin fixation and thus A/U rich sequences will be less accurately measured than G/C rich sequences (Masuda N, Ohnishi T, Kawamoto S, Monden M, Okubo K: Analysis of chemical modification of RNA from formalin-fixed samples and optimization of molecular biology applications for such samples, Nucleic Acids Res 1999, 27:4436-4443). Consequently, there will be gene specific differences in the efficiency and reproducibility of measuring mRNA in formalin-fixed tissues. In addition to its modification by formalin, the heavy fragmentation during the fixation and/or subsequent isolation process requires specialized primer design. Thus, there are severe limitations for PCR-based RNA measurements in formalin-fixed tissues. Alternative methods that are less sensitive to formalin-induced alterations are needed to improve the accuracy of RNA quantification (Bustin S A: Quantification of mRNA using real-time reverse transcription PCR(RT-PCR): trends and problems, J Mol Endocrinol 2002, 29:23-39; Bustin S A, Nolan T: Pitfalls of quantitative real-time reverse-transcription polymerase chain reaction, J Biomol Tech 2004, 15:155-166 Gunther E C, Stone D J, Gerwien R W, Bento P, Heyes M P: Prediction of clinical drug efficacy by classification of drug-induced genomic expression profiles in vitro, Proc Natl Acad Sci USA 2003, 100:9608-9613).

Performance of quantitative PCR (QPCR) has faired poorly in quantitation of FFPE RNAs because it is generally limited to 75-85 bp amplicon size, and multiple pooled gene-specific primers are required (Cronin M, Pho M, Dutta D, Stephans J C, Shak S, Kiefer M C, Esteban J M, Baker J B: Measurement of gene expression in archival paraffin-embedded tissues: development and performance of a 92-gene reverse transcriptase-polymerase chain reaction assay, Am J Pathol 2004, 164:35-42). QPCR requires a much greater purity of RNA than the bDNA assay and thus more steps to process the samples prior to analysis compared to the bDNA technology. After dewaxing, the RNA needs to be digested with Proteinase K, isolated and submitted to 1-2 times of DNAase I treatment to remove DNA contamination. A second problem that affects RNA quantification by QPCR is the required reverse transcription step to convert mRNA sequences of interest to cDNA. This enzymatic reaction is impeded by formalin-induced base modifications, by secondary mRNA structure and by impurities in the RNA preparation. Factors inhibiting reverse transcription will vary amongst FFPE tissue blocks. Although, introduction of a high temperature heating step during PCR amplification steps may partially reverse some of the RNA base modifications, for many samples these modifications are irreversible. Older samples are often so impaired that a decrease in average QPCR signal is >90%, requiring more input RNA and increasing Ct values to 35-40 (Masuda N, Ohnishi T, Kawamoto S, Monden M, Okubo K: Analysis of chemical modification of RNA from formalin-fixed samples and optimization of molecular biology applications for such samples, Nucleic Acids Res 1999, 27:4436-4443). With all these problems, QPCR has not been a satisfactory method of quantitating RNAs from FFPE samples.

In view of the above, a need exists for a faster and simpler way to harvest nucleic acids from embedded clinical tissue samples. It would be desirable to have a way to obtain nucleic acids from formalin fixed paraffin embedded samples without the use of hazardous solvents. The accuracy of nucleic acid analyses would benefit from a more quantitative and less damaging methods of nucleic acid extraction. Benefits can be obtained from methods to adjust analyses to take target degradation into consideration. The present invention provides these and other features that will be apparent upon review of the following.

SUMMARY OF THE INVENTION

Methods of the invention are useful in addressing problems encountered in analysis of nucleic acid samples that are physically difficult to process or have experienced degradation. The methods can help obtain good representative test materials from samples that were previously processed for evaluation of histopathology. The methods can increase the accuracy and sensitivity of sample analyses by providing more representative standard materials. The condition of possibly degraded nucleic acids can be determined by an inventive offset bDNA assay configured for increased sensitivity to target fragmentation. The methods can improve estimates of mRNA copy counts for test materials derived from unknown numbers of normal and/or abnormal cells. The techniques can be used in combination to optimize nucleic acid analyses of, e.g., test materials derived from normal and/or aneuploid cells, formalin fixed cells, paraffin embedded cells, aged clinical samples, and the like.

Methods of the invention include combinations of inventive techniques working together to enhance the sensitivity and accuracy of a nucleic acid determination. For example, mRNA copy numbers can be estimated accurately by determining the number of cells in a test sample (e.g., by comparing a test sample rDNA value to a standard function of rDNA versus cell number), preparing a standard function for an RNA assay (e.g., assay output versus a degraded in vitro RNA standard assay input—degradation of sample or standard determined, e.g., by an offset bDNA assay), determining an amount of a test mRNA in the test sample using the RNA assay standard function, and determining the copy number of the mRNA in the test cells based on the number of cells and the determined amount of test mRNA. This procedure can effectively determine mRNA copy numbers in a variety of cell and tissue types, such as, e.g., tumor cells, cell lines, cells from a microscope slide, clinical samples more than a year old, fresh tissue, freshly fixed cells, freshly fixed paraffin embedded tissues, cells fixed with formalin, cells embedded in paraffin, normal and/or aneuploid cells, and the like e.g., originating from humans, plants, or animals.

In one embodiment of the inventive techniques, a fast, simple, quantitative and reliable technique is provided to release nucleic acids from samples, such as formalin fixed paraffin embedded (FFPE) clinical samples, embedded in a matrix of hydrophobic media. In a general aspect, a method of collecting a nucleic acid from cells associated with a hydrophobic component can include suspending the sample, incubating the sample and separating nucleic acids from the sample and hydrophobic component. The sample of cells or tissue with the hydrophobic component melting at a temperature greater than 40° C. can be suspended in an aqueous solution. The suspension can be incubated at a temperature higher than 40° C. under conditions substantially non-denaturing to double stranded DNA of the cells, so that the hydrophobic component melts and the nucleic acid is released from the cells into the aqueous solution. Finally, the aqueous solution can be physically separated from the hydrophobic component, after the incubation, to collect the nucleic acid released from the cells.

This method of nucleic acid release or solubilization can work well for many cell and/or tissue samples. For example, the methods can be used to prepare aqueous test materials useful in analyses of DNA, a degraded nucleic acid, RNA, and the like. The methods are particularly useful to provide test samples for nucleic acid analysis of clinical samples containing a wax such as formalin fixed paraffin embedded tissue or cells.

Suspending the cells or tissue in the aqueous solution can be by an appropriate technique. For example, a tissue sample on a microscope slide can be scrapped off into an Eppendorf tube and vortexed. Thicker or more stubborn samples can be broken into smaller particles, e.g., by grinding, chopping, pressing, douncing, milling, and the like. The aqueous solution can include constituents designed to help disrupt the cells and tissues, to aid in the solubilization of the nucleic acids, and/or to condition the solution for the intended analysis. For example, the aqueous solution (water containing a solute) can include PEG, SDS, SSC buffer, NaHPO4, EDTA, denatured salmon sperm DNA, divalent cations, formamide, SSPE buffer, blocking probes, capture extenders, label extenders, preamplifiers, label probes, amplification probes, amplification multimers, a protease, a lipase, a surfactant, or nuclease inhibitor, and/or the like. In a preferred embodiment, the aqueous solution optionally contains a protease, such as proteinase K, at 10 ul/ml, 50 ul/ml, 100 ul/ml, 150 ul/ml, 250 ul/ml, 500 ul/ml, 1 mg/ml, or more.

Incubation in the method is for a time and temperature suitable to release the desired nucleic acid from the sample in an amount and concentration adequate for the intended analysis. Using associated methods of the invention, complete release of all nucleic acids from the sample is often not required because analyses can be standardized and normalized to provide meaningful results. In typical embodiments, the incubation is carried out at a temperature ranging from about 35° C. to about 99° C., from about 45° C. to about 95° C., from about 52° C. to about 90° C., from about 60° C. to less than 80° C., or about 65° C. Preferably, the incubation temperature is above the melting point of a predominant sample hydrophobic component by at least a couple of degrees, but below the Tm of the sample DNA under the conditions of the suspension. Incubation can be rapid, particularly at higher temperatures or for delicate or fine samples. Incubation time can be more than 20 minutes, or range from about 30 minutes to about 3 days or more, from about 1 hour to 1 day, from about 3 hours to about 18 hours, or 12 hours. In preferred embodiments, the incubation can be started in the afternoon and proceed over night for analysis in the morning. Methods of the invention allow a certain lack of precision in many sample handling steps due to the ability of the methods to correct for handling variables.

In many embodiments, the aqueous solution and incubation conditions do not include nucleic acid denaturing conditions, e.g., conditions that would melt most of the sample DNA from double stranded form to single stranded form. Denaturing conditions, as well known in the art, can include increased solution temperature, high pH, and high ionic strength.

Separating the hydrophobic component from the aqueous solution or suspension can be, e.g., by simple mechanical (e.g., solely physical) means. Although it has been the practice to separate paraffin from FFPE samples using chemical extractions (e.g., organic phase extractions), we find physical separation (e.g., mechanical manipulation without use of organic solvents) of the hydrophobic component to provide at least equivalent recovery of nucleic acids in the aqueous solution to produce test sample with less effort and hazard. Hydrophobic components tend to naturally segregate, e.g., driven by hydrophobic interactions, when exposed to the aqueous solutions and incubation conditions of the present invention. Typically, the hydrophobic component does not have the same density as the aqueous solution so a hydrophobic layer can form, e.g., above or below the suspension. This can be accelerated or affected by centrifugation. Such a layer can be separated from the aqueous layer by various physical means, e.g., by physically decanting the hydrophobic layer off the top, aspirating either the aqueous layer or hydrophobic layer away from the other, pipetting the layers from each other, solidifying the hydrophobic component at a temperature below the melting point so that it can be physically removed from the aqueous layer as a solid or semisolid. In preferred embodiments, the separation of the bulk of hydrophobic component from the sample does not include the use of organic extraction steps before the incubation step and/or after the incubation step.

Nucleic acids released from cells or tissues by the methods can be excellent test sample material for input to any number of nucleic acid analytical techniques. In many cases, the nucleic acids released into the aqueous solution can be captured on a solid support for detection by various assays known in the art. The solubilization methods, typically in combination with the complimentary methods further described herein, can be useful to provide accurate quantitation. To further purify the nucleic acids solubilized in the methods, for assays sensitive to disruption by cell lysate constituents, the separated solution can be phenol extracted and ethanol precipitated, as is known in the art. In preferred methods, the separated solution is analyzed, e.g., by a bDNA assay, without any organic extraction and/or denaturation steps (but with physical hydrophobic component separation). The released solutions of nucleic acids (typically, lysates) can provide good assay input material for various assays, including, e.g., bDNA analysis, northern blot analysis, Southern blot analysis, polymerase chain reaction, nucleic acid sequencing, agarose gel electrophoresis, differential display techniques, and the like.

In another aspect of the invention, test cell numbers represented in a lysate can be estimated based on the amount of a repetitive DNA that is rarely deleted or duplicated in the genome of a cell or tissue. The methods of determining a number of test cells can include, e.g., obtaining a reference nucleic acid sample from a known number of reference cells, quantitating the amount of a ribosomal DNA in the reference sample, providing a standard function (such as, a standard curve or a standard equation obtained through regression analysis) for the reference cell number versus the reference ribosomal DNA quantity, obtaining a test nucleic acid sample from test cells, quantitating the amount of the ribosomal DNA in the test sample, and determining the test cell number based on the standard function and the quantity of test ribosomal DNA.

Test cells and standard cells for determining cell number by the methods of the invention can be any of one or more type. The reference cells or the test cells requiring number determination can be, e.g., tumor cells, cells from a cell line, cells from a microscope slide, FFPE cells, normal cells, polyploid cells, and the like. In certain embodiments, the test cells have been lung tumor cells or colon tumor cells. In other cases, the test cells providing the reference nucleic acid sample have a substantially normal karyotype.

The preferred repetitive DNA for normalizations in the methods of determining test cell numbers is a ribosomal DNA. These DNAs are highly repetitive and are located on multiple chromosomes at positions less prone to translocations, deletions or insertions. Therefore, we have found them to be consistently represented in normal numbers, even in grossly aneuploid cell lines. In more preferred embodiments, ribosomal DNA is a 18S rDNA, a 5.8S rDNA, and/or a 28S rDNA.

The repetitive DNA can be quantitated (e.g., in a dilution series) for determination of a standard function, e.g., by any suitable technique, such as bDNA analysis, Southern blot analysis, polymerase chain reaction, agarose gel electrophoresis, and the like. The results can be used in comparison to test sample results to determine the number of cells represented in a test sample. For example, determining the test cell number can be by inputting the ribosomal DNA quantity of a test cell sample into the standard function, e.g., inputting the test ribosomal DNA quantity into: a formula comprising a ratio of cells to rDNA, a computer with analytical software; or into a comparison to a standard value on a standard curve. Using the determined test cell number, results of other analyses can be normalized to the cell number—for example, normalizing an mRNA assay result to copies per cell.

Standard functions determined based on known cell numbers and repetitive DNA can also be used to determine an efficiency of solubilization when the number of cells in a test sample is known. For example, the efficiency of a test nucleic acid extraction can be determined from the known number of test cells in a solubilized lysate compared to the number of test cells calculated from the standard curve to be represented in the test cell lysate.

In a further aspect of the invention, RNA that has been degraded can be more accurately quantitated using a degraded in vitro transcribed (IVT) RNA standard curve. For example, mRNA copy numbers can be determined by determining a number of cells in a test sample, preparing a standard function for an RNA assay output versus a degraded in vitro RNA standard assay input, determining an amount of a test mRNA in the test sample by the RNA assay using the standard function, and determining the copy number of the mRNA in the cells based on the number of cells and the determined amount of test mRNA. In a preferred embodiment, the appropriate degraded IVT RNA standard can be selected or the slope of a standard curve can be modified according to the results of an offset bDNA assay (described below).

In another aspect of the invention, the level of fragmentation of a bDNA target nucleic acid can be determined by an assay wherein capture extenders and label extenders are offset from each other along a target nucleic acid. For example, fragmentation of a target nucleic acid (having a target sequence unknown to be full length or fragmented to some extent) can have fragmentation detected by analyzing a sample of the nucleic acid in an offset bDNA assay wherein each of one or more offset capture extender probe C3 sequences are complimentary to sequences along the nucleic acid, and where one or more offset label extender L1 sequences are complimentary to sequences of the nucleic acid at positions spaced at least one nucleotide base either 5' or 3' from all the C3 complimentary sequences. With such a bDNA assay configuration, less signal can be generated if the nucleic acid is fragmented between the C3 and L1 complimentary sequences than if the nucleic acid is not fragmented between the C3 and L1 complimentary sequences. For example, less signal can be generated if a significant portion of the nucleic acid is in a fragmented form.

In many cases, the offset assay can be made more accurate and reliable by having an appropriate control assay run on the sample using a standard bDNA assay having interspersed capture extenders and lapel extenders. For example, a sample of the nucleic acid can be analyzed in a second bDNA assay wherein two or more control capture extender probe C3 sequences are complimentary to sequences at different positions along the nucleic acid, and where one or more control label extender L1 sequences are complimentary to sequences at different positions along the nucleic acid sequence with one or more of the control L1 sequences being complimentary to the nucleic acid at positions between the positions complimentary to two or more of the control C3 sequences. The ratio of the control assay result over the offset assay result will be higher if the nucleic acid is fragmented than the ratio if the nucleic acid is not fragmented.

The offset assay can be more sensitive when the label extenders are further offset from the capture extenders along the target nucleic acid. In preferred embodiments, the nucleic acid sequences complimentary to the offset C3 sequences are separated from the nucleic acid sequences complimentary to the offset L1 sequences by a space of 75% or more of the nucleic acid nucleotides (that is, based on the full length target nucleic acid, the space between the nearest LE and CE sites would be at least 75% of the target nucleic acid length). Describing the CE/LE spacing another way, it is preferred the offset label extender L1 sequences be complimentary to sequences of the nucleic acid spaced at least 25 nucleotide bases 5' and/or 3' from all the C3 complimentary sequences. In preferred embodiments, no L1 complimentary sequence is between any two C3 complimentary sequences.

In other aspects of the offset bDNA assay technology, blocking probes having sequences complimentary to sequences of the target in the space between LE and CE compliments are included during hybridization, e.g., to reduce assay background signals.

The output of offset bDNA assays and ratios to controls can characterize the condition of a sample. For example, the offset assay signal, or ratio to control, can be correlated to the average length of the target nucleic acid sequences. The fragmentation level thus provided can be used, e.g., to select an assay standard or to select a standard function for use in RNA quantitation versus a degraded IVT RNA standard.

DEFINITIONS

Unless otherwise defined herein or below in the remainder of the specification, all technical and scientific terms used herein have meanings commonly understood by those of ordinary skill in the art to which the present invention belongs.

Before describing the present invention in detail, it is to be understood that this invention is not limited to particular processes or analytical methods, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a component" can include a combination of two or more components; reference to "a nucleic acid" can include mixtures of nucleic acids, and the like.

Although many methods and materials similar, modified, or equivalent to those described herein can be used in the practice of the present invention based on the present specification without undue experimentation, many preferred materials and methods are described herein. In describing and claiming the present invention, the following terminology will be used in accordance with the definitions set out below.

The term "about" as used herein indicates the value of a given quantity varies by +/−10% of the value, or optionally +/−5% of the value, or in some embodiments, by +/−1% of the value so described.

The term "polynucleotide" (and the equivalent term "nucleic acid") encompasses any physical string of monomer units that can be corresponded to a string of nucleotides, including a polymer of nucleotides (e.g., a typical DNA or RNA polymer), peptide nucleic acids (PNAs), modified oligonucleotides (e.g., oligonucleotides comprising nucleotides that are not typical to biological RNA or DNA, such as 2'-O-methylated oligonucleotides), and the like. The nucleotides of the polynucleotide can be deoxyribonucleotides, ribonucleotides or polymers of nucleotide analogs, can be natural or non-natural, and can be unsubstituted, unmodified, substituted or modified. The nucleotides can be linked by phosphodiester bonds, or by phosphorothioate linkages, methylphosphonate linkages, boranophosphate linkages, or the like. The polynucleotide can additionally comprise nonnucleotide elements such as labels, quenchers, blocking groups, or the like. The polynucleotide can be, e.g., single-stranded or double-stranded.

A "polynucleotide sequence" or "nucleotide sequence" is a polymer of nucleotides (an oligonucleotide, a DNA, an RNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

Two polynucleotides "hybridize" when they associate to form a stable duplex, e.g., under relevant assay conditions. Nucleic acids hybridize due to a variety of well characterized physico-chemical forces, such as hydrogen bonding, solvent exclusion, base stacking and the like. An extensive guide to the hybridization of nucleic acids is found in Tijssen (1993) Laboratory Techniques in Biochemistry and Molecular Biology-Hybridization with Nucleic Acid Probes, part I chapter 2, "Overview of principles of hybridization and the strategy of nucleic acid probe assays" (Elsevier, New York).

The term "complementary" refers to a polynucleotide that forms a stable duplex with its "complement," e.g., under relevant assay conditions. Typically, two polynucleotide sequences that are complementary to each other have mismatches (mismatched base pairs) at less than about 20% of the bases, at less than about 10% of the bases, preferably at less than about 5% of the bases, one mismatch, and more preferably have no mismatches.

A "capture extender" or "CE" is a polynucleotide (or comprises a nucleotide) that is capable of hybridizing to a nucleic acid of interest and to a capture probe. The capture extender typically has a first polynucleotide sequence C-1, which is complementary to the capture probe, and a second polynucleotide sequence C-3, which is complementary to a polynucleotide (target) sequence of the nucleic acid of interest. Sequences C-1 and C-3 are typically not complementary to each other. The capture extender is preferably single-stranded.

A "capture probe" or "CP" is a polynucleotide that is capable of hybridizing to at least one capture extender and that is tightly bound (e.g., covalently or noncovalently, directly or through a linker, e.g., streptavidin-biotin or the like) to a solid support, a spatially addressable solid support, a slide, a particle, a microsphere, a bead, or the like. The capture probe typically comprises at least one polynucleotide sequence C-2 that is complementary to polynucleotide sequence C-1 of at least one capture extender. The capture probe is preferably single-stranded.

A "label extender" or "LE" is a polynucleotide that is capable of hybridizing to a nucleic acid of interest and to a label probe system. The label extender typically has a first polynucleotide sequence L-1, which is complementary to a polynucleotide sequence of the nucleic acid of interest, and a second polynucleotide sequence L-2, which is complementary to a polynucleotide sequence of the label probe system (e.g., L-2 can be complementary to a polynucleotide sequence of an amplification multimer, a preamplifier, a label probe, or the like). The label extender is preferably single-stranded.

A "label" is a moiety that facilitates detection of a molecule (e.g., by providing a detectable signal). Common labels in the context of the present invention include fluorescent, luminescent, light-scattering, and/or calorimetric labels. Suitable labels include enzymes and fluorescent moieties, as well as radionuclides, substrates, cofactors, inhibitors, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Many labels are commercially available and can be used in the context of the invention.

A "label probe" or "LP" is a single-stranded polynucleotide that comprises a label (or, optionally, that is configured to bind to a label) that directly or indirectly provides a detectable signal. The label probe typically comprises a polynucleotide sequence that is complementary to the repeating polynucleotide sequence M-2 of an amplification multimer; however, if no amplification multimer is used in the bDNA assay, the label probe can, e.g., hybridize directly to a label extender.

A "label probe system" comprises one or more polynucleotides that comprise one or more labels and one or more polynucleotide sequences M-1, each of which is capable of hybridizing to a label extender. The label provides a signal, directly or indirectly. Polynucleotide sequence M-1 is typically complementary to sequence L-2 in the label extenders. The one or more polynucleotide sequences M-1 are optionally identical sequences or different sequences. The label probe system can include a plurality of label probes (e.g., a plurality of identical label probes) and an amplification multimer; it optionally also includes a preamplifier or the like, or optionally includes only label probes, for example.

An "aqueous solution", as used herein, refers to an aqueous solution (water containing one or more solutes) suitable to retain a nucleic acid of interest in solution. For example, an aqueous solution can have a pH and ionic strength conducive to dissolving and holding a nucleic acid in solution. Aqueous solutions of the invention can optionally include constituents useful in releasing nucleic acids from cells and tissues, such as, e.g., pH buffers, salts, surface active agents and/or proteases. Aqueous solutions optionally include constituents that are useful as components of a nucleic acid assay or hybridization, such as, e.g., formamide, a sodium chloride-sodium citrate (SSC) buffer, nucleic acid probes, and the like.

A "hydrophobic component" associated with a cell or tissue sample is a compound substantially insoluble in water (e.g., less than 1% soluble in pure water). Typical hydrophobic components associated with samples are lipids, fats, oils, hydrocarbons, waxes, hydrophobic membrane components, and the like. In certain embodiments of the invention, the hydrophobic component is a paraffin, e.g., clinical sample embedding wax.

"Physically separating", as used herein, refers to separation of a hydrophobic component layer from an aqueous solution layer by physical means. Organic extraction of a hydrophobic component from an aqueous suspension of a sample is considered a chemical separation of the hydrophobic component, e.g., from a FFPE sample and is not considered to be physical separation, even at the point when the organic extraction phase is removed from the remaining aqueous phase. Physical separation is generally a mechanical procedure to remove the hydrophobic component (in solid, semisolid or liquid form) from contact with the aqueous solution, e.g., by grasping, pushing, sucking, aspirating, pouring, blowing, filtering, adsorbing, absorbing, pulling, and/or the like. Separation can include removing the hydrophobic component from the aqueous solution or removing the aqueous solution from the hydrophobic component.

As used herein, a "standard function" is a function, or expression of a function, that represents a relationship between two assay parameters, such as, e.g., a known assay input and the resulting output. The output can be a raw data output or a value (such as, a number of molecules or concentration of an analyte) derived from the output. Standard functions and their expressions (e.g., standard curves) are well known in the art. The standard function can be in the form of an algebraic function (e.g., equation for a line) or can be provided in the form of a standard curve (e.g., resulting from regression analysis) on an X-Y chart. The standard function can also be expressed as a ratio, constant, or algorithm (e.g., in the form of computer software).

BRIEF DESCRIPTION OF THE DRAWINGS

FIG. 1 is a block flow diagram of a prior art dewaxing protocol using organic solvents (e.g., Dewax) and phase extraction techniques to remove paraffin from formalin fixed paraffin embedded clinical samples before initiation of nucleic acid solubilization "homogenization" protocols.

FIG. 2 shows an exemplary solubilization ("homogenization") protocol of the invention wherein preliminary dewaxing of the sample is not required and paraffin is ultimately separated from the aqueous nucleic acid homogenate (lysate) by a single non-extraction, non-denaturing physical separation step.

FIGS. 4A to 4E show examples of ribosomal DNAs (rDNAs) retaining substantially consistent representation in various normal cells, aneuploid cells, and tumor cells.

FIG. 5 shows bDNA assay standard curves demonstrating a linear response between cell line cell number and assay signal output for rDNAs.

DETAILED DESCRIPTION

Figure 3:
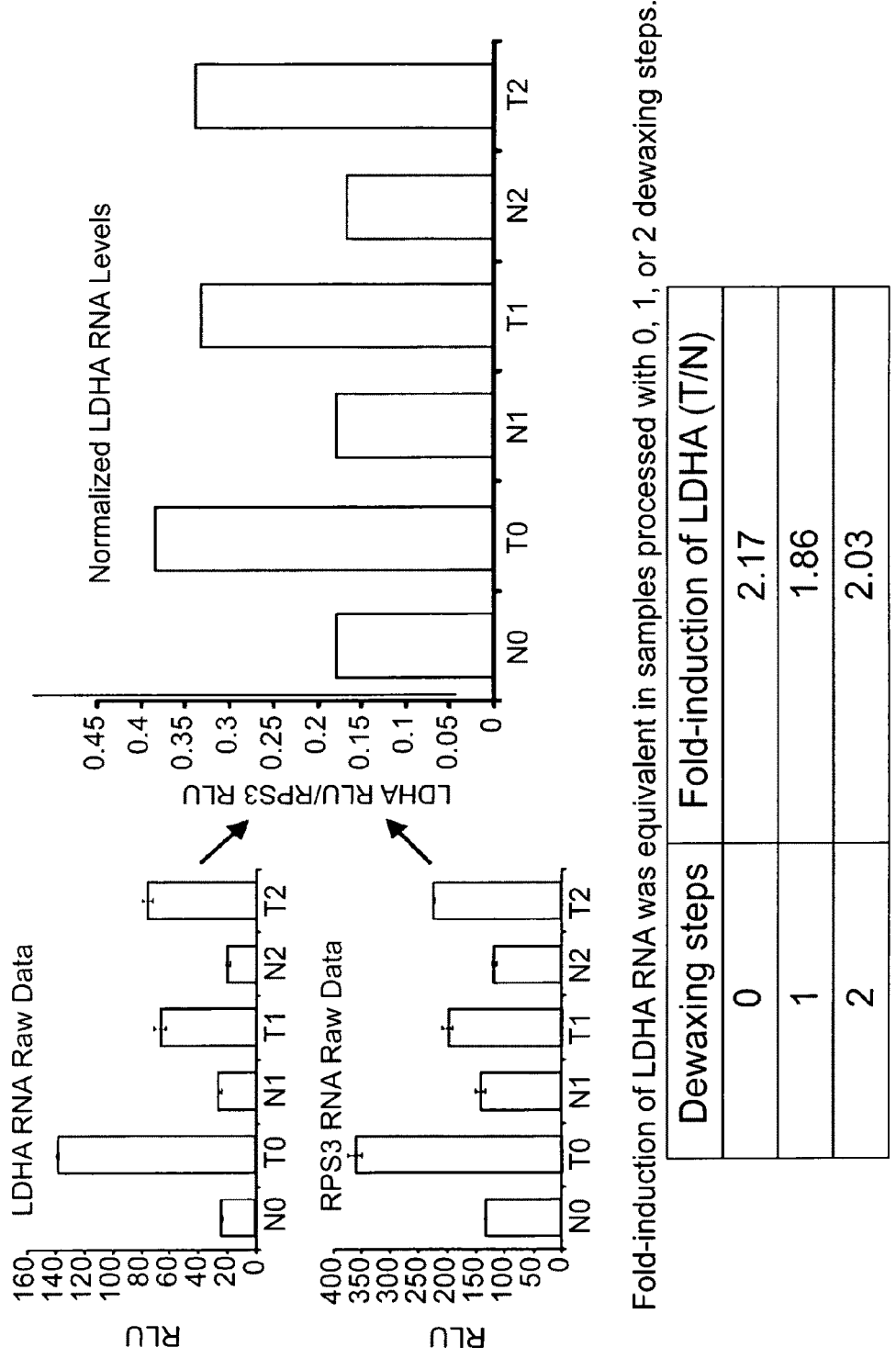
FIG. 3 shows a graphic representation of mRNA expression induction. Fold-induction determinations of LDHA mRNA levels in tumor cells over normal cells are found to be substantially the same using post-solubilization separation of hydrophobic components from lysate as for the old art organic phase extraction before homogenization (lysate preparation).
Figure 4B:
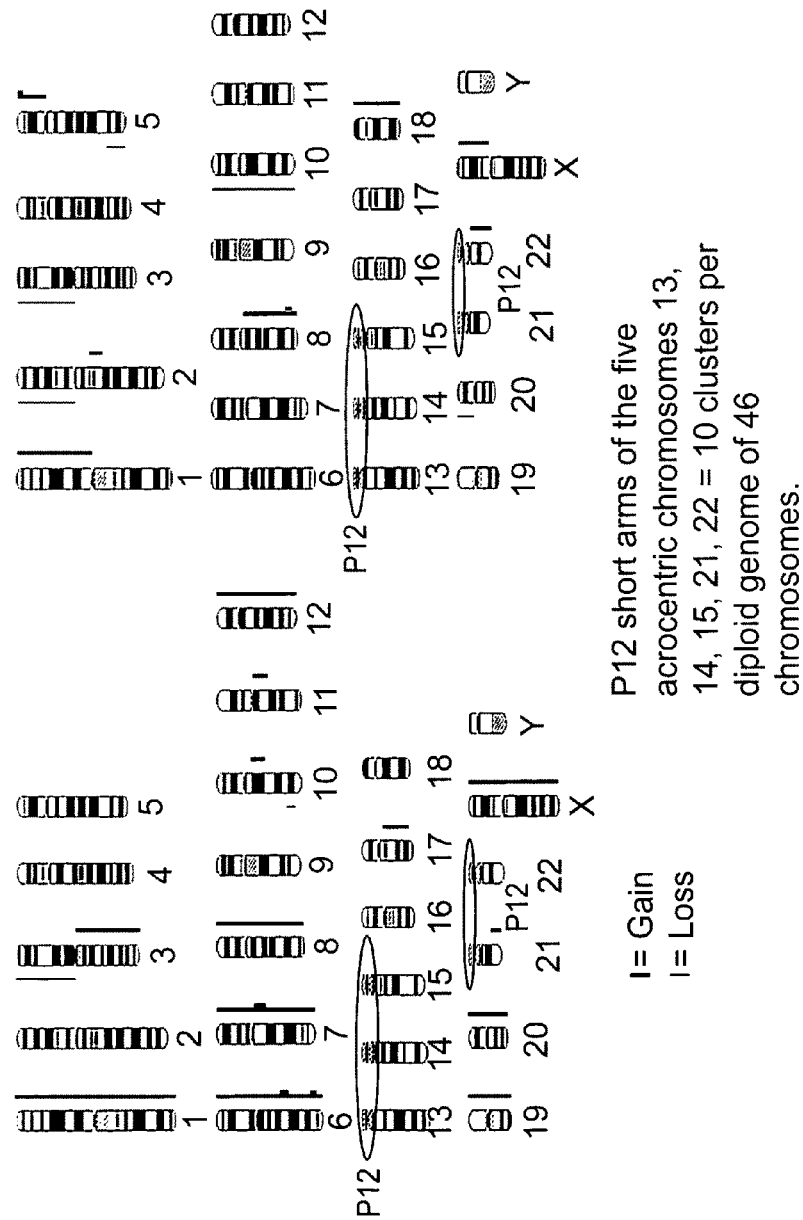
Figure 4C:
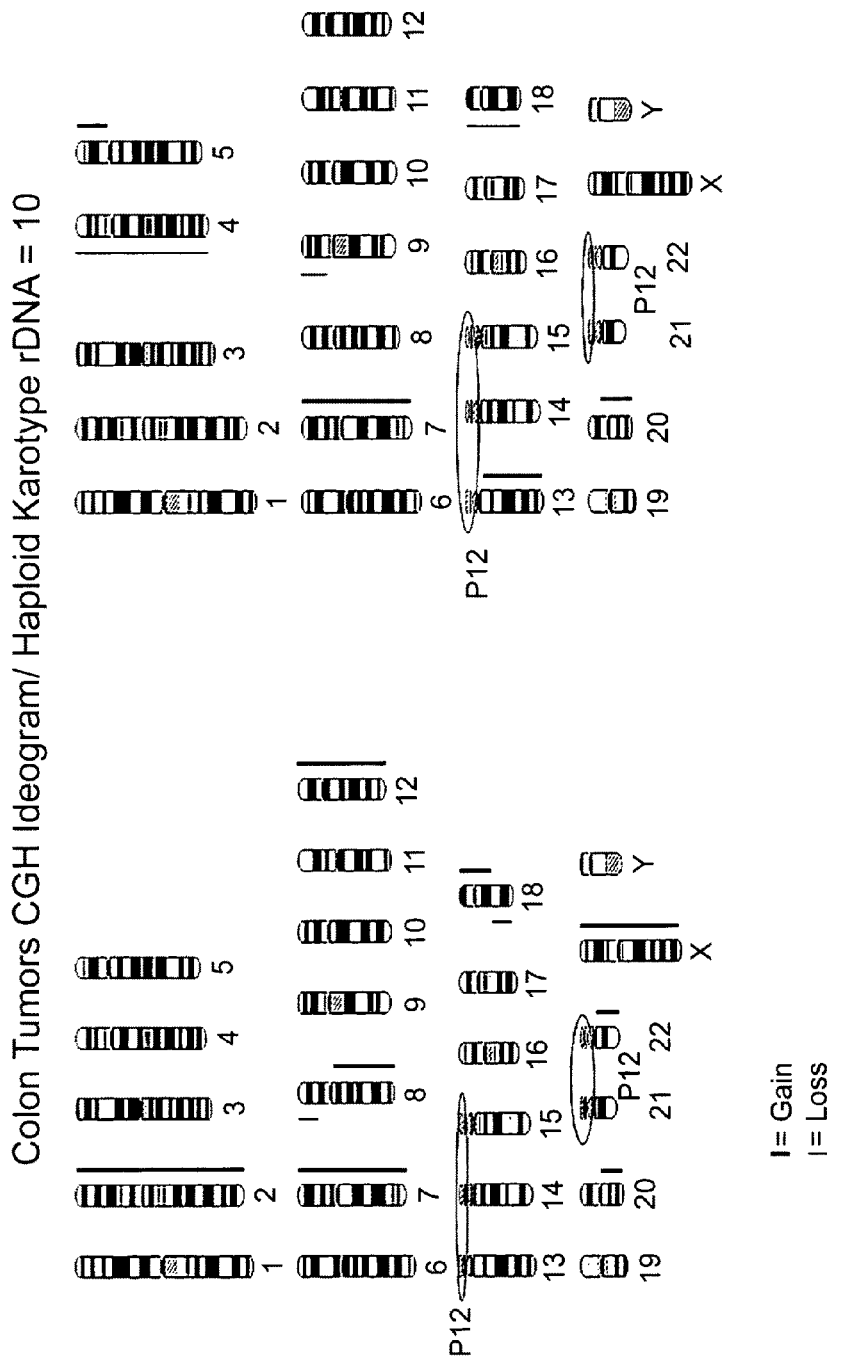
Figure 4D:
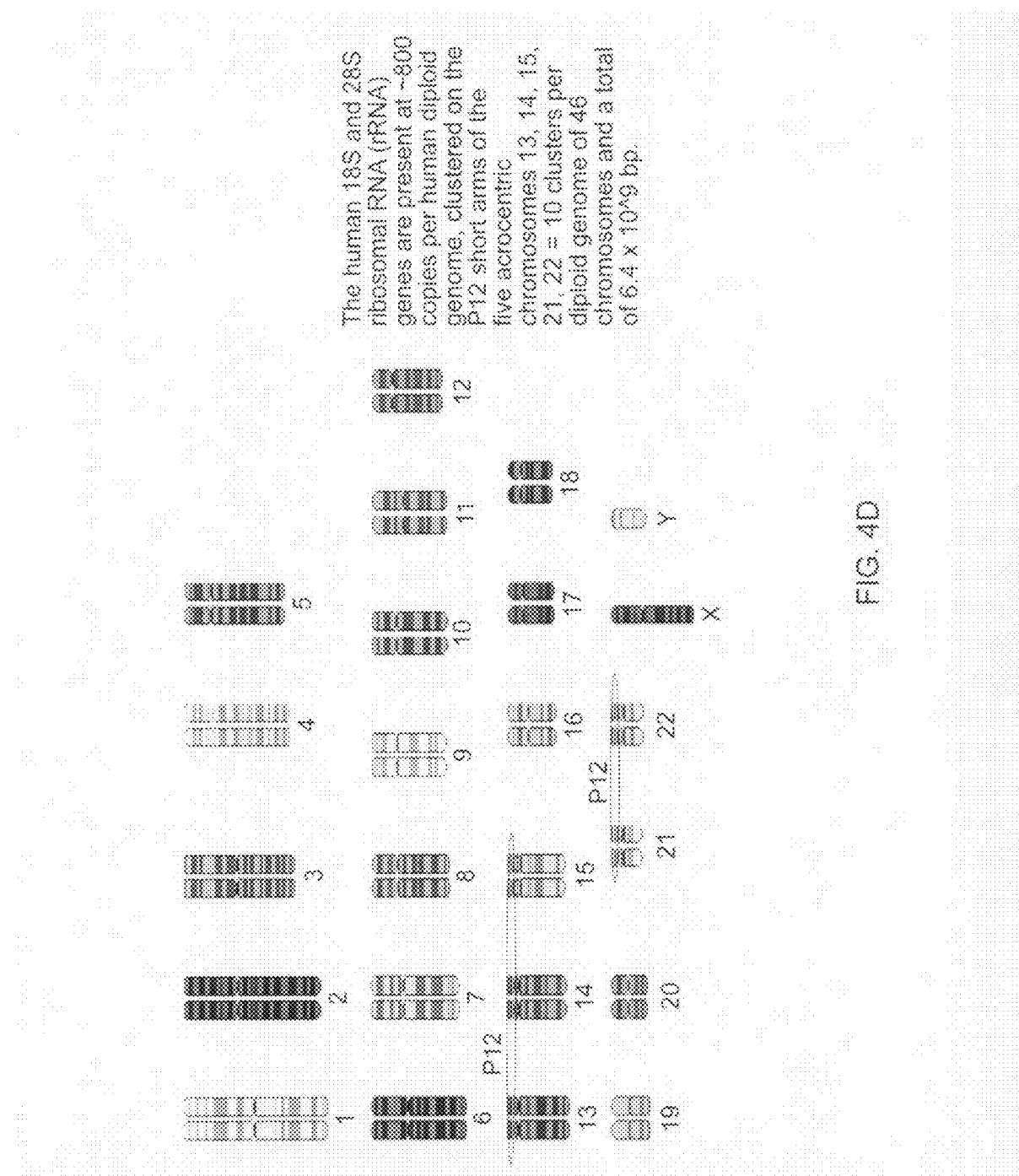
Figure 4E:
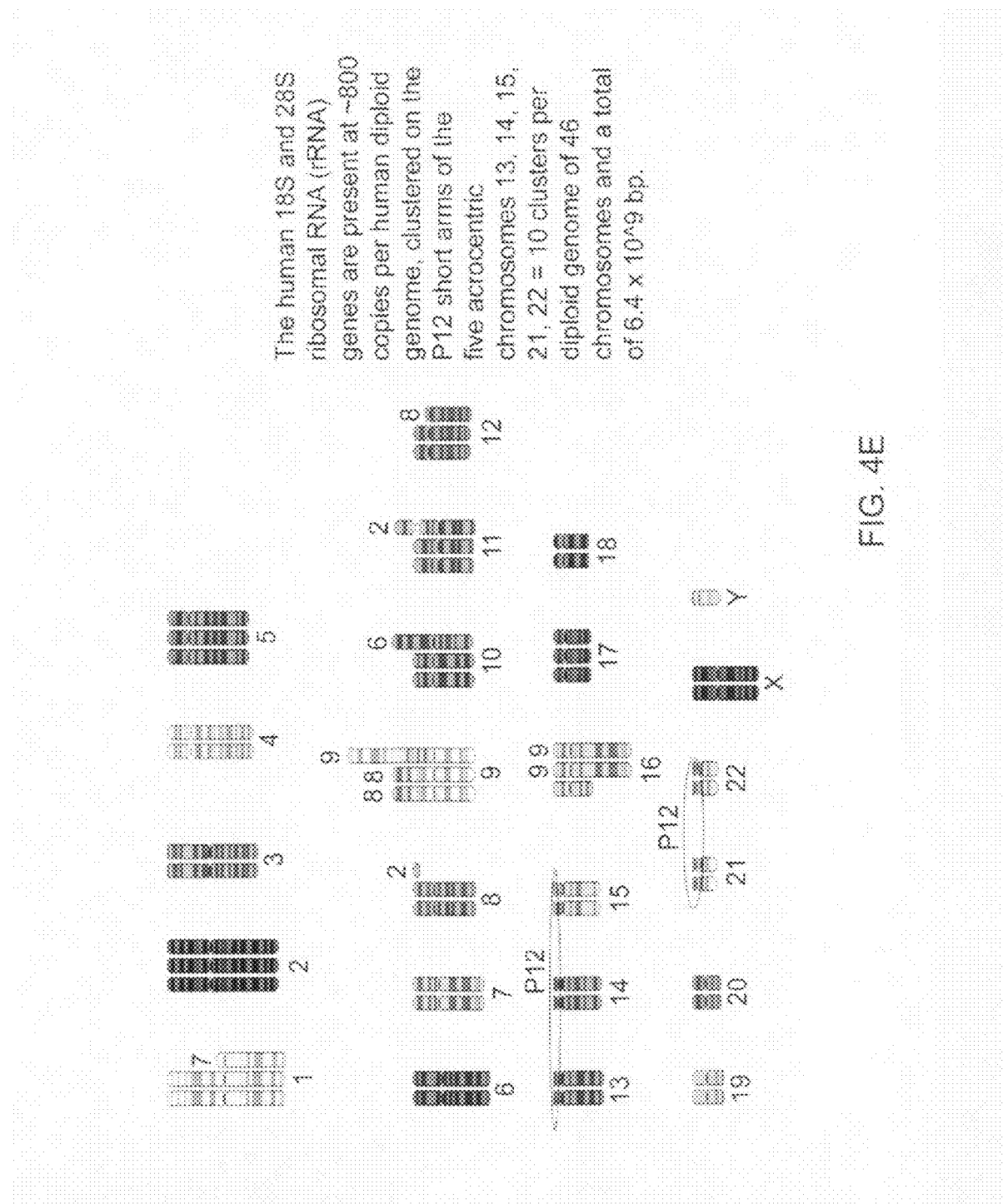

The present invention is directed to methods of collecting and quantitating nucleic acids from cells and tissues. Cells, previously processed, e.g., by formalin fixation and paraffin embedding, can be suspended in an aqueous homogenization solution at elevated temperatures under non-denaturing conditions so that nucleic acids are released from cells into lysate solution separate from the paraffin material. The number of source cells and the efficiency of nucleic acid extraction can be accurately determined by a normalization based on a ribosomal DNA reference. The copy number of an mRNA per cell can be more accurately determined using analyses normalized with an appropriately degraded in vitro transcribed (IVT) RNA standard material. An estimation of sample RNA degradation can be provided, e.g., by comparing bDNA signals from control assays wherein capture and label sites are dispersed along an RNA target against a signal for a test assay wherein capture sites are on one end of the target RNA separated from label sites on the other end of the target RNA, as will be discussed below.

Prior art methods of determining nucleic acids in embedded clinical samples required repeated organic chemical extractions (dewaxing) before solubilization of nucleic acids from the sample. The present invention eliminates the requirement for such an extraction step altogether. Scraped-off sections or chunks of tissue in a paraffin block can be directly solublized by, e.g., adding 300 μL Homogenizing Solution (Panomics Fremont Calif.) supplemented with Proteinase K (0.3 mg/mL) per 60-100 microns (25-250 mm$^2$) pooled tissue sections or 10 mg unsectioned tissue from a block and digested overnight at 65° C. Paraffin than can separate from the tissue homogenate during overnight Proteinase K digestion at 65° C. and, if abundant, forms a visible layer above aqueous homogenate. Liquid paraffin can be physically removed with a pipettor or allowed to solidify at room temperature during centrifugation, pierced, and the solubilized material (lysate) physically removed from underneath the hydrophobic component, e.g., by aspiration. The aqueous lysate solution can be transferred to a fresh microfuge tube for immediate use or stored at −80° C. for future use. The present invention significantly improves the accuracy and simplifies quantification of RNA or DNA from formalin fixed paraffin embedded (FFPE) samples.

A major difficulty in studying differential gene expression by cells, such as those of FFPE samples, is how to normalize for gene heterogeneity. The gene transcript number (mRNA copies) is typically expressed as a copy number per cell. Unfortunately, counting of cells is not practical for many FFPE tissues or cell slides. In many cases, the copy number calculations have been normalized based on total DNA or total RNA recovered from the sample. However, total cellular DNA and RNA content can increase or decrease, e.g., with tumor aneuploidy (Jacques B de Kok, Rian W Roelofs, Belinda A Giesendorf, Jeroen L Pennings, Erwin T Waas, Ton Feuth, Dorine W Swinkels and Paul N Span, Laboratory Investigation (2005) 85, 154-159). Thus, it has not been known how to accurately quantify the number of cells represented in a FFPE sample. We have found that one possibility is to normalize based on a gene or genes identified as not affected by tumor aneuploidy. Preferably, the genes are represented as multiple copies in the genome to increase the sensitivity of detection. Furthermore, it is preferred that the gene or genes be stable and distributed across multiple chromosomes, so that loss or gain of some of the genes on any one chromosome would have less of an effect on the overall cell number determination.

About 30% of the human genome consists of repeated sequences (Britten, R. J. & Kohne, D. E. (1968) Science 161, 529-540), of which over half are repeated more than $10^5$ times per genome. Some of these repeated sequences are organized in long, tandem arrays, while others are interspersed among less frequently represented sequences including structural genes. A number of human interspersed repeated DNA sequence families have been identified. The largest family consists of $3 \times 10^5$ copies of related sequences, each about 300 nucleotides long, with most members having a site that can be cleaved by the restriction endonuclease Alu I (Rubin, C. M., Houck, C. M., Deininger, P. L., Friedmann, T. & Schmid, C. W. 1980 Nature 284, 372-374). Other, less frequently represented, short, interspersed repeated sequences (SINES) have been reported by Deininger et al. (Deininger, P. L., Jolly, D. J., Rubin, C. M., Friedmann, T. & Schmid, C. W. (1981) J. Mol. Biol. 151, 17-33.) and Miesfeld et al. (Miesfeld, R., Krystal, M. & Arnheim, N. (1981) Nucleic Acids Res. 9, 5931-5947). Adams et at (Adams, J. W., Kaufman, R. E., Kretschmer, P. J., Harrison, M.& Nienhuis, A. W. (1980) Nucleic Acids Res. 8, 6113-6127) reported a longer interspersed repeated DNA sequence (LINES) family that is 6,400 nucleotides long on the average and are represented some $4 \times 10^3$ times per genome. These repetitive DNA sequences are known to mediate or enhance the rate of recombination in the genomes of many organisms (Jelinek and Schmid 1982; Hardman 1986; Vogt 1990), whereby the interspersed repetitive DNA consists of repeat units dispersed throughout the genome. Mispairing between such repeats has been shown to be a frequent cause of deletions and duplications (Smita M. Purandare, and Pragna I. Patel, 199: 773-786 Genome Res.) and thus are often not practical to use to determine the cell number in FFPE tissue samples.

Of more practical use are the human 5.8S, 18S and 28S ribosomal RNA (rRNA) genes (rDNA), present at ~800 copies per human diploid genome, clustered on the P12 short arms of the five acrocentric chromosomes 13, 14, 15, 21, 22; for 10 clusters per diploid genome of 46 chromosomes and a total of $6.4 \times 10^9$ bp. (Worton, R. G., Sutherland, J., Sylvester, J. E., Willard, F. H., Bodrug, S., Dube, I., Duff, C., Kean, V., Ray, N. P. and Schmickel, R. D. (1988), Science, 239, 64-68). Each ribosomal gene is part of a 43 kb repeat unit that can be divided into two regions: a 13.3 kb transcribed region which contains the highly conserved genes for 18S, 5.8S and 28S rRNA subunits of the ribosome, and a 30 kb non-transcribed spacer (NTS) (Gonzalez, L. I., Wu, S., Li, W., Kuo, A. B. and Svlvester, E. J. (1992) Nucleic Acids Res., 20, 5846-5847.) Repeat unit clusters consist of head-to-tail arrays of 80 repeats (Sakai, K., Ohta, T., Minoshima, S., Kudoh, J., Wang, Y., De Jong, J. P. and Shimizu, N. (1995)).

The NCBI has established the SKY/M-FISH and CGH database to provide a public platform for investigators to share and compare their molecular cytogenetic data. The karyotypes of hundreds of tumors can be viewed on the SKY/comparative genomic hybridization database website. This database is a part of the Cancer Chromosome Aberration Project sponsored by the National Cancer Institute (Kirsch, I. R., Green, E. D., Yonescu, R., Strausberg, R., Carter, N., Bentley, D., Leversha, M. A., Dunham, I., Braden, V. V., Hilgenfeld, E., Schuler, G., Lash, A. E., Shen, G. L., Martelli, M., Kuehl, W. M., Klausner, R. D., and Ried, T. Nat. Genet., 24: 339-340, 2000). In addition, the complete karyotypes for 59 cell lines can be viewed on the internet, including representative images of the cell line karyotypes (Anna V. Roschke, Giovanni Tonon, Kristen S. Gehlhaus, Nicolas McTyre, Kimberly J. Bussey, Samir Lababidi, Dominic A. Scudiero, John N. Weinstein, 2 and Ilan R. Kirsch CANCER RESEARCH 63, 8634-8647, 2003).

After viewing individual tumor karyotypes (lung, colon, breast, etc.) and 59 cell line karyotypes for their ribosomal DNA content, we determined here that ribosomal DNA gene content varied very little in the primary tumors, which is do in part to the fact that the ribosomal genes are clustered on the P12 short arms of the five acrocentric chromosomes and thus the loss or gain of any one short arm equals only 10% divergence from the normal tissue ribosomal gene dosage. Since the ploidy and total DNA of each cell line and tumor varies, while the ribosomal DNA number varies less, we have found that more accurate cell number estimates can be obtained using normalization by ribosomal DNA.

In another aspect of the invention, an mRNA copy number for cells, e.g., previously embedded in a microscope slide, can be determined with enhanced accuracy by normalization according to a similarly degraded RNA standard. The cell number represented in the post-homogenization separated solution of nucleic acids from the embedded cells can be determined based on a standard function (e.g., a standard curve) of cell number versus a quantity of repetitive DNA (such as a ribosomal DNA). The amount of the mRNA can be determined for the solution of nucleic acids based on, e.g., a standard curve of degraded IVT RNA versus an RNA assay (such as, e.g., bDNA) output. The accuracy of such a copy number determination can be improved by consideration of extraction efficiency from the repetitive DNA data and mRNA normalization by the degraded RNA curve, as discussed herein.

For many methods of the invention, bDNA technology is a preferred nucleic acid quantitative technique. bDNA technology is fortunate in not being subject to many of the problems of QPCR in quantitation of RNAs. In fact the hybridization step in bDNA assays can be facilitated by formalin-modification of RNA. In addition, impurities that reduce the activity of reverse transcriptase and DNA polymerase in QPCR can be inconsequential in the branched chain assay since this assay does not require enzymatic activities, but relies instead on hybridization. To overcome the problems of RNA degradation and fragmentation, a unique approach of probe design has been developed for the bDNA assay (Wen Yang, Botoul Maqsodi, Yunqing Ma, Son Bui, Kimberly L. Crawford, Gary K. McMaster, Frank Witney, and Yuling Luo, Direct quantification of gene expression in homogenates of formalin-fixed, paraffin-embedded tissues Biotechniques, Vol. 40, No. 4 (2006), pp 481-486; Warrior U, Fan Y, David C A, Wilkins J A, McKeegan E M, Kofron J L, Burns D J: Application of QuantiGene nucleic acid quantification technology for high throughput screening, J Biomol Screen 2000, 5:343-352; Bushnell S, Budde J, Catino T, Cole J, Derti A, Kelso R, Collins M L, Molino G, Sheridan P, Monahan J, Urdea M: ProbeDesigner: for the design of probesets for branched DNA (bDNA) signal amplification assays, Bioinformatics 1999, 15:348-355. Many methods of the present invention provide ways to improve bDNA analyses, and other quantitative nucleic acid assays, with regard to problematic samples.

Collecting Nucleic Acids from FFPE Tissue Samples

In order to obtain sensitive, quantitative and reliable assay results for nucleic acids from cells and tissues, it is important to harvest a useful amount of the nucleic acid substantially free of physically and chemically interfering substances. This problem can be particularly difficult for samples, such as paraffin embedded clinical samples that are associated with hydrophobic preservatives and waxy supporting matrices. In the present invention, we have found that reliable and quantitative separation of cells and tissue contents from hydrophobic sample components can be accomplished, e.g., by breaking the sample into particles of small size, suspending the particles in an appropriate lysis solution containing a protease, incubating the suspension at a temperature above the melting temperature of the hydrophobic component to release the nucleic acids into an aqueous phase and generate a separate hydrophobic component phase, and separating the aqueous phase from the hydrophobic phase.

Obtaining Small Particles of the Cell or Tissue Sample

If the cell or tissue sample is not already in the form of small particles or sheets with a high surface to volume ratio, it is usually beneficial to break the sample into smaller bits so that nucleic acids can be extracted into an aqueous solution in a relatively quantitative and timely fashion. Samples, such as dried cell bulks, embedded tissues, formalin fixed paraffin embedded cells or tissues, clinical samples stored on microscope slides, and the like, can be reduced to a fine powder or paste, using any appropriate methods known in the art, to enhance the harvest of nucleic acids from the sample.

For example, the samples can be chopped, ground, milled, scrapped, dounced, homogenized, sheared, and/or the like, to particle sizes reasonably adapted to nucleic acid release from cells and tissues by the methods of the invention. For example, the samples can be broken into particles of average diameter less than 1 mm, less than 0.1 mm, less than 10 um, less than 1 um, or less. In preferred embodiments, the samples are broken down to particles about 100 times the volume of the cells, 10 times the volume of the cells, or about the size of the cells.

The samples can be physically and/or chemically broken down to the appropriate size in the presence of a liquid matrix, or not. The liquid matrix can be an aqueous solution with components suitable for introduction into later handling and/or analysis steps. For example the liquid matrix can provide a suitable environment for an enzymatic reaction or a stringent nucleic acid hybridization.

Suspension of Particles in an Aqueous Solution

Sample particles are placed in an aqueous solution for treatments that release nucleic acids from the sample cells into the solution forming a lysate. The aqueous solution can be as simple as water to dissolve the nucleic acids. Typically the aqueous solution includes ingredients that increase the solubility of the nucleic acids, disintegrate cell/tissue structures that interfere with release of the nucleic acids, and/or provide a suitable environment for analysis of the nucleic acids.

The aqueous solution can include constituents useful to later analytical procedures and/or storage conditions. For example, the aqueous solution can include constituents of a nucleic acid hybridization buffer, e.g., PEG, SDS, SSC buffer, NaHPO4, EDTA, denatured salmon sperm DNA, formamide, SSPE, etc. The aqueous solution can include bDNA constituents, such as, e.g., blocking probes, capture extenders, label extenders, preamplifiers, label probes, amplification probes, amplification multimers, and the like. In preferred embodiments for release of nucleic acids from many formalin treated or paraffin embedded samples, the aqueous solution can include one or more of: a protease, lipase, surfactant, or nuclease inhibitor.

The sample particles can be suspended in the aqueous homogenization solution while the sample is being broken up into small particles. For example, the sample can be ground, milled or dounced in the presence of the desired aqueous solution. Alternately, the sample can be, e.g., dry ground and transferred into a aqueous solution after particle sizing. Alternately, the particles can be, e.g., centrifuged or filtered from a liquid matrix used for sizing the particles and exchanged over to the desired aqueous solution for suspension and release of nucleic acids (e.g., by dialysis, diafiltration, resuspension after centrifugation or filtration, etc.).

The sample particles can be suspended in the aqueous solution to expose the particles to conditions that release nucleic acids. The suspension can be made by, e.g., stirring, douncing, vortexing, inverting, mixing, shaking, or simply by introducing the particles to the solution. Although the mixture often starts as a suspension of particles, most or all of the sample material typically ends up in solution or in a hydrophobic layer by the end of suspension and incubation treatments.

In preferred embodiments, the aqueous solution is a solvent for nucleic acids and is an appropriate assay solution for an intended nucleic acid assay. For example, the aqueous solution can provide conditions of pH, ionic strength, viscosity, surface active agents, blocking agents, etc, suitable for attachment of the nucleic acids to a solid support (such as a blotting membrane) or for stringent hybridization of the nucleic acid with one or more nucleic acid targets or probes.

In many cases, it is desirable to include one or more proteases in the aqueous homogenization solution. Significant amounts of the desired nucleic acid are often entrapped by the proteins and protein matrices of cells and tissues. Proteases can help disrupt these proteins and help release the nucleic acids. In preferred embodiments, the protease is a proteinase K, e.g., at a concentration of more than 50 ug/ml, 100 ug/ml, 150 ug/ml, 200 ug/ml, 300 ug/ml, 500 ug/ml, or more.

Incubating the Suspension

The suspension of the sample in the aqueous solution can be incubated at or above the melting temperature of one or more sample hydrophobic components. The incubation can melt and release the hydrophobic component from the sample material and disintegrate cell and/or tissue structures to form an aqueous lysate containing nucleic acids of interest.

Hydrophobic components of samples can include lipids, fats and/or oils naturally present in the sample of cells or tissue, or not. Hydrophobic components typically of most concern in analysis of nucleic acids from clinical samples are preservative and embedding compositions processed into the sample to aid in the preservation, handling, and/or storage of the samples. Commonly encountered hydrophobic components with regard to samples used in methods of the invention are cell and tissue embedding media, such as paraffin embedding waxes.

Incubation of the suspension is preferably under conditions non-denaturing to the genomic DNA of the sample. The conditions of temperature, ionic strength, pH, divalent cation concentration, formamide concentration, and the like, well known in the art, can be significantly less than conditions that would denature (melt) a preponderance of the DNA in the sample (see Rapley, R. and Walker, J. M. eds., *Molecular Biomethods Handbook* (Humana Press, Inc. 1998). For example, the Tm of a DNA-DNA duplex can be estimated using the following equation:

$$Tm(° C.)=81.5° C.+16.6(\log_{10}M)+0.41(\% G+C)-0.72(\% f)-500/n,$$

where M is the molarity of the monovalent cations (usually Na+), (% G+C) is the percentage of guanosine (G) and cystosine (C) nucleotides, (% f) is the percentage of formamide and n is the number of nucleotide bases (i.e., length) of the hybrid. Tm increases with higher ionic concentrations of the solvent due to the stabilizing effects that cations have on DNA duplex formation. More cations bind to duplex DNA than to the component single strands. Different cations may have different effects on Tm. The most common monovalent cation is Na+; however, from a Tm standpoint, sodium and potassium are functionally interchangeable. Divalent cations (such as Mg++) also stabilize DNA hybrids (increase Tm) but their effects are quantitatively much different from monovalent cations. Increased pH can increase charge repulsion between DNA strands and thus lower the Tm. In preferred embodiments, the incubation temperature during solubilization is at least 2° C., 5° C., or 110° C. below the Tm for DNA of the sample in the suspension.

The suspension can be incubated at a temperature above the melting temperature of one or more hydrophobic components present in the sample. For example, the suspension can be incubated at a temperature ranging from about 40° C. to about 100° C., from about 41° C. to about 95° C., from about 45° C. to about 90° C., from about 50° C. to about 80° C., from about 60° C. to about 70° C., or about 65° C. Preferred incubation temperatures are at least above the melting temperature of the highest melting hydrophobic component or the most abundant hydrophobic component in the sample. Preferred incubation temperatures are temperatures also supporting the desired activity of enzymes, such as proteases in the solution. For clinical samples embedded in paraffin, the melting point can be, e.g., between about 43° C. and 71° C., more commonly between 52° C. and 64° C., depending on chain lengths and degree of refinement. We have found that most embedded clinical samples include paraffin that is readily melted and separated from the aqueous solutions at a temperature of 65° C.

Suspensions of samples can be incubated for a time adequate to release sufficient amounts of a nucleic acid to carry out a desired analysis. The time can vary depending on, e.g., the amount of connective fibers in a tissue, the incubation temperature, the activity of proteases, the amount of paraffin present, the amount and type of surface active agents present, the presence of physical factors (such as agitation), the sensitivity of the desired nucleic acids (and the presence or absence of destructive nuclease enzymes and/or their inhibitors), pH, ionic strength, and the like. Suspension incubation times can range, e.g., from less than about 30 minutes to 5 days, 3 hours to 3 days, from about 6 hours to about 2 days, from about 9 hours to about 1 day, or about 12 hours (e.g., over night). We have found that high yields of approximately 90% nucleic acid release can be accomplished in over night incubations, according to methods of the invention.

Physically Separating the Aqueous Solution from the Hydrophobic Component

In methods of the invention, the hydrophobic component is repelled by the aqueous solution, and thus tends to self-segregate under the influence of the solutions and incubation conditions of the invention. Moreover, the hydrophobic component typically has a density different (e.g., lower) from the aqueous solution, and thus will tend to float above the aqueous solution, e.g., when released from the sample by methods of the invention. Once the hydrophobic component is segregated from the rest of the suspension, the hydrophobic component can be physically separated from sample constituents remaining in the aqueous solution.

In some cases, the hydrophobic component can be separated from the aqueous lysate solution containing released nucleic acids after incubation, by simply aspirating it off the top of the incubation container. Alternately, the incubated suspension can be chilled to a temperature below the melting point of the hydrophobic component and it can be mechanically removed as a solid or the lysate efficiently decanted or aspirated from under it.

It is often useful to centrifuge the incubated suspension into separate layers with different densities. For example, an incubated suspension can be centrifuged at from 1000×g to about 20,000×g for from 1 minute to about 1 hour to separate the suspension into, e.g., a bottom cell/tissue debris layer, a middle lysate layer and a top hydrophobic component layer. Such centrifugation can have the benefit of more discretely and more quantitatively segregating hydrophobic components that may be in the form of a colloid or suspension of fine lipid globules. Centrifugation can provide discrete layers, such as clarified lysate layers, that can be readily removed by routine liquid handling procedures, e.g., without resort to chemical extraction procedures.

The lysate of aqueous solution with solublized cell/tissue constituents, including nucleic acids, can be separated from the hydrophobic component, and from any cell debris, by other techniques known in the art. For example the incubated suspension can be filtered through a membrane of appropriate materials and pore size. Debris and/or solidified hydrophobic component can be retained by the filter membrane while clarified lysate passes through the membrane. Wet hydrophilic membranes can pass the lysate while retaining the hydrophobic component due to hydrophobic repulsion. Hydrophobic membranes can pass the lysate while adsorbing and retaining the hydrophobic component.

In some embodiments, hydrophobic components segregated from the sample during incubation of the suspension can be removed in an organic extraction (chemical separation), such as a xylene or phenol extraction. In preferred embodiments, separating the hydrophobic components does not require an organic extraction step. This is often the case when, e.g., the lysate is to be used in a bDNA assay.

Lysates obtained from samples according to the methods of the invention can be compatible test materials for analysis by any number of nucleic acid assay techniques. In many cases, intelligent selection of aqueous solution constituents and separation techniques can result in samples ready for direct input to assays, such as bDNA analysis, northern blot analysis, Southern blot analysis, polymerase chain reaction, spectrophotometry, fluorometry, nucleic acid sequencing, agarose gel electrophoresis, and the like. In other cases, the lysate can be adjusted as necessary, e.g., buffer exchange procedures or by addition of buffers, substrates, etc., to accommodate a particular assay. In the case of FFPE lysates, accuracy of assay results can be enhanced, e.g., by normalization for sample extraction efficiency and/or analyte degradation using techniques of the invention described below.

Quantitation of Nucleic Acids Based on a Multicopy DNA Standard

When cell lysates are prepared from clinical samples, particularly tissue samples or embedded samples, it may be unclear how many cells have released their contents into the lysate. Although it has been known to normalize a lysate harvest according to the amount of total DNA present, this determination can introduce errors, e.g., due to inconsistent DNA content among various cells. We have found that certain repetitive genes, spread among various chromosomes, and preferably on the short arms of acrocentric chromosomes can be used to provide consistent and accurate cell number estimates, even in the context of certain aneuploid cells, such as cell lines and tumor cells.

Cell numbers represented in a lysate can generally be better estimated by normalizing relative to a repetitive gene (preferably a ribosomal gene) that exists on two or more different chromosomes at a site near the centromere (such as on a short arm of an acrocentric chromosome). It can be beneficial if the repetitive gene exists in a large number of copies, e.g., to enhance sensitivity of their detection. Here, we have identified ribosomal genes, particularly genes encoding 18S, 28S and 5.8S ribosomal RNAs, as excellent reference genes for normalizing cell numbers represented in lysates, e.g., of common aneuploid cells.

The methods of using rDNAs to provide a cell count can be employed in association with any number of quantitative assays involving any cell constituent. For example, the molecular copy number of any analyte (e.g., a nucleic acid, a protein, or a small molecule) can be calculated based on the assayed analyte quantity and cell number derived based on rDNA analysis.

Providing a Standard Function of Cell Number to rDNA

To determine the number of test cells represented in a lysate, one can, e.g., obtain data from which to derive a standard function of ribosomal DNA (rDNA) versus numbers of cells, and interpolate the number of cells represented in an unknown lysate based on the amount of the rDNA present. A standard function can be an equation expressing the relationship between one quantity and another, such as, e.g., an assay input and assay output, or a constant proportional relationship between a number of cells and an amount of RNA in a lysate of the cells. Typical standard functions can include, e.g., a standard curve plotting X-Y coordinates of related values on a chart, an equation established by regression analysis of standard assay results, or a constant ratio or proportion between related parameters. An expression of a standard function can be a "best fit" line on a paper chart; a ratio or line slope representing a proportionality between the cell numbers and their rDNA; an equation determined by regression analysis techniques; a result provided by a computer using an appropriate program, and the like, as is known in the art.

For example, the number of cells represented in a test lysate can be determined by: obtaining a reference lysate from a known number of cells; quantitating the amount of genes encoding a ribosomal RNA in the reference lysate; determining a ratio of cell numbers to an amount of the rDNA in a sample; quantitating the amount of the rDNA is a lysate of test cells; and, calculating the number of test cells represented in the test lysate based on the ratio.

The number of cells in a reference sample can be determined, e.g., by counting them using methods known in the art. For example reference cells grown in suspension can be counted in a hemocytometer, in a Coulter counter, by a cell sorter, inferred by packed cell volume, and the like. Cells in a reference tissue can be counted microscopically, inferred from tissue volume, or counted as for suspended cells above after release by mechanical, chemical and/or enzymatic techniques. The reference cells can be normal cells, primary culture cells, cell lines, cells released from tissues, cells from biological fluids, and/or the like. The reference cells can be the same type as the test cells, or not. The cells can be uniformly the same or a mixture of different cell types.

The test cells enumerated by the standard curve can be any type of interest. The test cells can be the same type of cells as the reference cells or at least derived from the same species of animal as the reference cells. In a preferred embodiment, a particular benefit is obtained wherein the test cells do not have to be the same type of cells as the reference cells. For example, in certain embodiments, the reference cells can be normal cells or mixtures of a variety of cells, while the test cells are aneuploid cells, cells from "immortal" cell lines, cancer cells, tumor cells, and the like.

Quantitating Nucleic Acids and Test Cell Numbers

Quantitating rDNAs in lysates to determine cell counts can be by any method with sufficient sensitivity and accuracy to provide a useful output. However, because errors in determination of both the reference rDNA and test rDNA carry over to contribute to the error of the final cell count result, it is preferred the nucleic acid quantitation method be precise and accurate. Typically, the rDNA determinations for both test and reference samples should use the same methodology, to avoid interassay variables, but the methods do not have to be the same.

Quantitation of rDNA in the present methods can be by, e.g., QPCR, bDNA analysis, Northern blot analysis, in situ hybridizations, and the like. With regard to determinations for lysates from formalin fixed, paraffin embedded samples, it is preferred to use bDNA techniques, which are not as sensitive to sample degradation and impurities.

Extraction Efficiency Calculations

In addition to determining unknown test cell counts described above (by comparing test lysate rDNA to the cell number versus rDNA according to a standard function), an extraction efficiency can be determined for lysis of test cells, based on the same standard curve.

In a situation where the number of test cells is known (e.g., by counting methods described above), the extraction efficiency can be determined for lysis of those cells. For example, the amount of an rDNA can be determined for the test lysate and the number of cells represented read from a standard curve, prepared as described above. The percent extraction efficiency can be calculated as 100 times the number of cells represented in the test lysate divided by the known number of cells processed to make the lysate. Such information can be useful, e.g., in optimizing a lysis technique or to normalize an analytical result.

Suppose a lysate of cells is to be assayed for the presence of an analyte and it is important how much of the analyte is present per cell, then the extraction efficiency can be used to improve the accuracy of the calculation by normalizing the analyte quantity to the actual number of cells. For example, in many circumstances, it is useful to know the expression levels of certain genes in cells. A known number of the cells can be lysed and a mRNA transcribed from the gene can be quantitated, e.g., by RT-PCR or bDNA methods. rDNA values for the lysate can be compared to a standard curve of cell number versus rDNA to find the number of cells represented in the lysate. The extraction efficiency can be expressed as the ratio of represented cells over the known number of cells. The amount of the mRNA per cell can be calculated as the total mRNA in the lysate divided by the known number of cells times the extraction efficiency.

Using a Degraded IVT RNA Curve to Determine mRNA Copy Numbers

Assay of degraded samples for nucleic acids often provides erroneous results. In particular, analysis of nucleic acids from aged samples or samples exposed to harsh treatments often results in weak signals and incorrectly low output values or false negative assay output. To solve this problem, we have determined that standard curves prepared using degraded in vitro transcribed (IVT) RNA can improve the accuracy of RNA assays carried out on such degraded samples.

Standard Functions for Degraded RNA

A standard function can be established to represent the relationship between the input of known amounts of a degraded IVT RNA and the output of a quantitative RNA assay. An unknown RNA, typically known or expected to be in a degraded form, can then be analyzed using the RNA assay to provide an output value. When the assay output for the unknown RNA is input to the standard function, the result can be a more accurate RNA quantity value than for a standard function provided, e.g., by regression analysis of a standard curve prepared using full length undegraded IVT RNA standard. If the unknown RNA sample came from a known number of cells, dividing the RNA quantity by the number of cells can provide a more accurate determination of the RNA copy number per cell.

A standard function can express the relationship between an amount of degraded RNA and the output of an RNA assay. The RNA assay can be any known in the art, such as, e.g., bDNA analysis, northern blot analysis, RT-polymerase chain reaction, agarose gel electrophoresis, and the like. The accuracy of the standard function can be enhanced, as is known in the art, by, e.g., obtaining standard data for increased numbers of standard concentrations, by testing each standard in higher numbers of replicates, by determining the standard quantities with higher accuracy, by using best fit regression analysis, and the like.

Standards and Test Samples

In vitro transcribed RNA is a preferred standard for many RNA analyses because large quantities of highly pure material can be obtained. Degraded IVT RNA can be obtained from full length undegraded IVT RNA by appropriate treatment. In preferred embodiments, the IVT RNA is degraded in the same fashion as the RNA to be analyzed, e.g., by age, light, chemicals, enzymes, heat, and/or the like. In many cases, fragmentation of the RNA is the type of degradation with the most significant effect on an assay. This is particularly true for many RNA analyses based on hybridization reactions with the test RNA. In preferred embodiments of the invention, an IVT RNA standard material is degraded by exposure to high pH, resulting in fragmentation comparable to the known or expected fragmentation of a test RNA sample.

It is envisioned that a standard function can be established for a quantitative RNA assay representing the relationship between assay output and sample input of RNA having various known degrees of degradation. Where the quantity of an RNA in a test sample is known, assay of the test sample with reference to the standard function can provide a result indicating the degree of degradation for the test RNA sample.

The quantity of an RNA, such as a degraded RNA, can be determined based on a quantitative assay and an standard function established using degraded RNA standards. The test sample RNA can be any type, such as, e.g., mRNA, rRNA, tRNA, IVT RNA, formalin (formaldehyde, methanol, water) treated RNA, RNA from dehydrated tissues, aged RNA (e.g., RNA from cells or tissue samples older than one year), RNA from human clinical samples, FFPE cell and tissue samples, RNA samples from microscope slides, RNA samples degraded by exposure to RNase enzymes, and the like.

Assay Results

The quantity determined for a test RNA can be expressed, e.g., in relative or absolute terms. The initial output value of an assay is typically in some unit of magnitude, such as, e.g., absorbance units, fluorescence units, relative light units (RLU), a voltage, a light intensity, a radioactive particle count, and the like. The assay value can be input to a standard function to output something more tangible, such as a quantity of associated RNA, e.g., a mass, weight, concentration, number of moles, number of nucleotide bases, number of molecules, etc.

The choice of degraded IVT RNA standard (or previously determined standard function) can be based on a known or expected degree of degradation in the test sample RNA. For example, based on experience with FFPE samples stored for different lengths of time (see, e.g., FIG. 18 agarose gels), one could select a standard with similar degradation for preparation of a standard curve. Alternately, the degree of degradation of sample RNA could be evaluated for the actual test sample by sizing techniques, such as, e.g., size exclusion chromatography, mass spectroscopy, gel electrophoresis, by offset bDNA analysis (discussed below), and the like. Quantitative results for analysis of degraded RNA can often be improved by selecting standard functions based on knowledge on hand.

Quantitative mRNA results determined using the degraded IVT RNA standard curve can be input to further calculations. For example, where the number of cells is known that were the source of the mRNA, the amount or number of molecules of the mRNA per cell can be calculated. It is envisioned that the number of cells represented by an RNA sample can be known, e.g., by counting the cells, as discussed above, or can be determined, e.g., based on an rDNA assay with reference to an appropriate standard curve of cells versus rDNA.

Determining Nucleic Acid Degradation by Comparing Interspersed and Offset Probe Systems A control bDNA assay for a nucleic acid with multiple capture extender (CE) complimentary target sequences dispersed along the nucleic acid, and multiple label extender (LE) complimentary target sequences interspersed along the nucleic acid, can generate a strong signal, even if the nucleic acid is highly fragmented. In contrast, a test bDNA assay with all or most of the CE target sequences at one end of the nucleic acid sequence and all or most of the LE target sequences spaced away at the other end of the nucleic acid sequence can fail to generate a signal, e.g., if the tested nucleic acid is fragmented at a point in the space between the CE and LE targets. This signal difference, dependent on the LE and CE target sequence locations can be utilized in assays to estimate the degree of fragmentation for a nucleic acid.

bDNA Assays bDNA assays can generally be described as, e.g., capture of a target nucleic acid by a capture extender associated with a solid support, the target being decorated at one or more point with label extenders typically associated with branched DNA molecules capable of binding a multitude of label probes to generate a large signal.

For example, in one aspect of bDNA analysis, a target nucleic acid is captured and its presence on the solid support is detected using a labeled branched-chain DNA (bDNA—amplification multimer). Detecting the presence of the target nucleic acid on the solid support can include hybridizing a first set of one or more label extenders (typically, two or more label extenders) and a label probe system comprising a label to the first target nucleic acid and detecting the presence of the label on the solid support. The label probe system typically includes an amplification multimer and a plurality of label probes. The amplification multimer is capable of hybridizing simultaneously to a label extender and to a plurality of label probes. The label probe can include the label, or it can be configured to bind to the label. Suitable labels include, but are not limited to, an enzyme or a fluorescent label. When an enzyme (e.g., alkaline phosphatase) is used as the label, its activity can be detected with a chemiluminescent, colorimetric, or similar technique, as is well-known in the art. When a fluorescent label is used, detecting the presence of the label on the solid support typically comprises detecting a fluorescent signal from the label.

Figure 17:
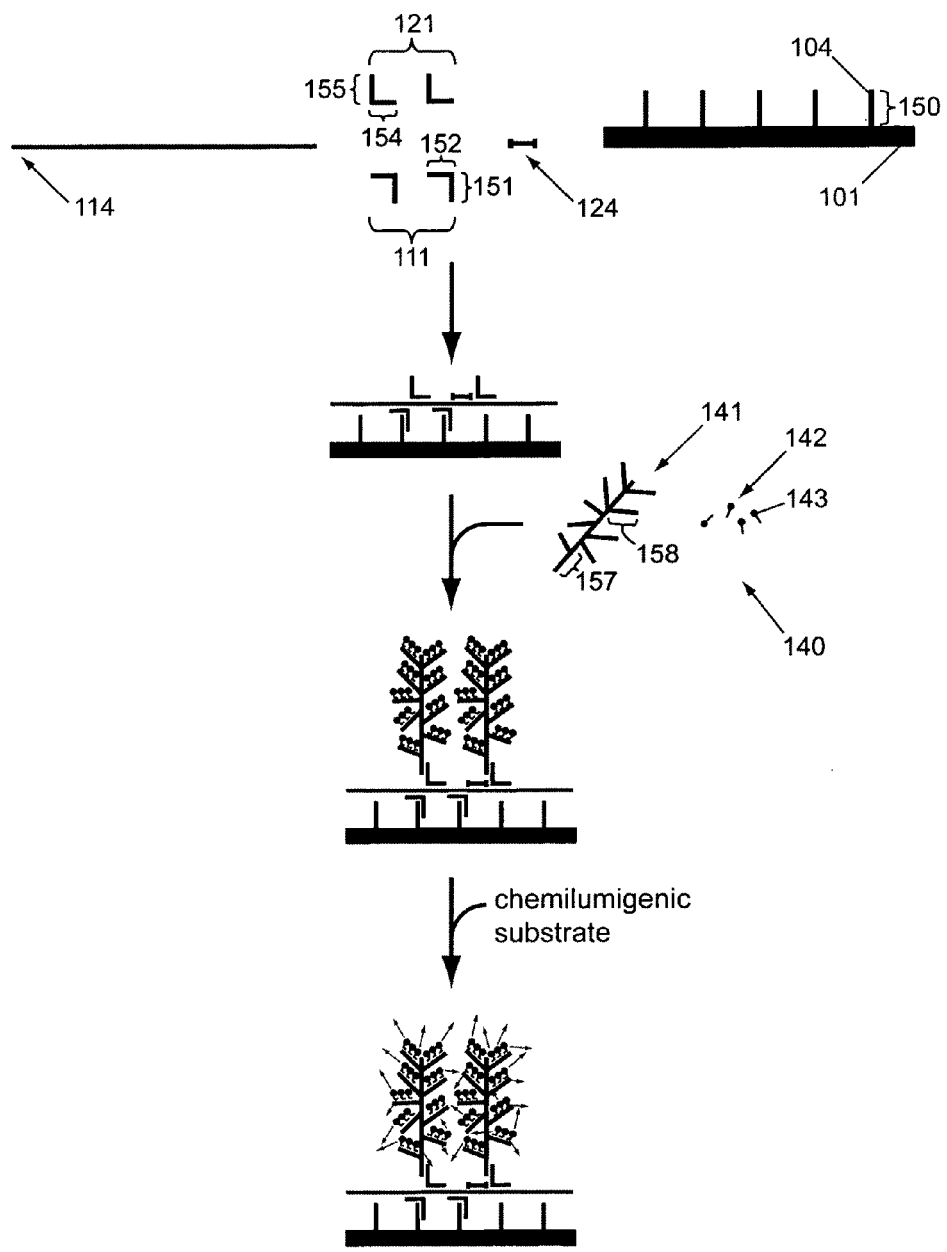
FIG. 17 shows a schematic diagram of an exemplary bDNA assay system.

An exemplary embodiment in which a single target nucleic acid is captured and detected using a bDNA assay is schematically illustrated in FIG. 17. A sample of cells or tissue is lysed to produce a lysate including target nucleic acid 114. The target nucleic acid 114 (e.g., an mRNA whose expression is to be detected) is captured by capture probe 104 on solid support 101 (e.g., a well of a microtiter plate) through set 111 of synthetic oligonucleotide capture extenders. Each capture extender has a first polynucleotide sequence C-3 (152) that can hybridize to the target nucleic acid and second polynucleotide sequence C-1 (151) that can hybridize to the capture probe through sequence C-2 (150) in the capture probe. Typically, two or more capture extenders are used; optionally, one CE can be used to capture a target. Each label extender in label extenders set 121 hybridizes to a different sequence on the target nucleic acid, through sequence L-1 (154) that is complementary to the target nucleic acid, and to sequence M-1 (157) on amplification multimer (141), through sequence L-2 (155). Blocking probes (124), which hybridize to sequences in the target nucleic acid not bound by either capture extenders or label extenders, are often used in bDNA assays to reduce non-specific target probe binding. A probe set for a given target nucleic acid thus consists of capture extenders, label extenders, and optional blocking probes 124 for the target nucleic acid. The capture extenders, label extenders, and optional blocking probes are complementary to nonoverlapping sequences in the target nucleic acid, and are typically, but not necessarily, contiguous. In this example, a single blocking probe is used; typically, an array of different blocking probes is used in an optimized bDNA assay.

Signal amplification can begin with the binding of the label extenders to the target nucleic acid. The amplification multimer is then hybridized to the label extenders. The amplification multimer has multiple copies of sequence M-2 (158) that is complementary to label probe 142 (it is worth noting that the amplification multimer is typically, but not necessarily, a branched-chain nucleic acid; for example, the amplification multimer can be a branched, forked, or comb-like nucleic acid or a linear nucleic acid). Label 143, for example, alkaline phosphatase, is covalently attached to each label probe. (Alternatively, the label can, e.g., be noncovalently associated with the label probes.) In the final step, labeled complexes are detected, e.g., by the alkaline phosphatase-mediated degradation of a chemilumigenic substrate, e.g., dioxetane. Luminescence is reported as relative light units (RLUs) on a microplate reader. The amount of chemiluminescence is proportional to the level of target nucleic acid originally present in the sample (a relationship describable with a standard function).

In the preceding example, the amplification multimer and the label probes comprise label probe system 140. In another example, the label probe system also comprises a preamplifier, e.g., as described in U.S. Pat. No. 5,635,352 and U.S. Pat. No. 5,681,697, which further amplifies the signal from a single target mRNA. In yet another example, the label extenders hybridize directly to the label probes and no amplification multimer or preamplifier is used, so the signal from a single target mRNA molecule is only amplified by the number of distinct label extenders that hybridize to that mRNA.

Basic bDNA assays have been well described and have been used, e.g., to detect and quantify mRNA transcripts in cell lines and to determine viral loads. The bDNA assay provides direct quantification of nucleic acid molecules at physiological levels. Several advantages of the technology distinguish it from other DNA/RNA amplification technologies, including linear amplification, good sensitivity and dynamic range, great precision and accuracy, simple sample preparation procedure, and reduced sample-to-sample variation. For additional details on bDNA assays, see, e.g., U.S. Pat. No. 4,868,105 to Urdea et al. entitled "Solution phase nucleic acid sandwich assay"; U.S. Pat. No. 5,635,352 to Urdea et al. entitled "Solution phase nucleic acid sandwich assays having reduced background noise"; U.S. Pat. No. 5,681,697 to Urdea et al. entitled "Solution phase nucleic acid sandwich assays having reduced background noise and kits therefore"; U.S. Pat. No. 5,124,246 to Urdea et al. entitled "Nucleic acid multimers and amplified nucleic acid hybridization assays using same"; U.S. Pat. No. 5,624,802 to Urdea et al. entitled "Nucleic acid multimers and amplified nucleic acid hybridization assays using same"; U.S. Pat. No. 5,849,481 to Urdea et al. entitled "Nucleic acid hybridization assays employing large comb-type branched polynucleotides"; U.S. Pat. No. 5,710,264 to Urdea et al. entitled "Large comb type branched polynucleotides"; U.S. Pat. No. 5,594,118 to Urdea and Horn entitled "Modified N-4 nucleotides for use in amplified nucleic acid hybridization assays"; U.S. Pat. No. 5,093,232 to Urdea and Horn entitled "Nucleic acid probes"; U.S. Pat. No. 4,910,300 to Urdea and Horn entitled "Method for making nucleic acid probes"; U.S. Pat. No. 5,359,100; U.S. Pat. No. 5,571,670; U.S. Pat. No. 5,614,362; U.S. Pat. No. 6,235,465; U.S. Pat. No. 5,712,383; U.S. Pat. No. 5,747,244; U.S. Pat. No. 6,232,462; U.S. Pat. No. 5,681,702; U.S. Pat. No. 5,780,610; U.S. Pat. No. 5,780,227 to Sheridan et al. entitled "Oligonucleotide probe conjugated to a purified hydrophilic alkaline phosphatase and uses thereof"; U.S. patent application Publication No. US2002172950 by Kenny et al. entitled "Highly sensitive gene detection and localization using in situ branched-DNA hybridization"; Wang et al. (1997) "Regulation of insulin preRNA splicing by glucose" Proc Nat Acad Sci USA 94:4360-4365; Collins et al. (1998) "Branched DNA (bDNA) technology for direct quantification of nucleic acids: Design and performance" in Gene Quantification, F Ferre, ed.; and Wilber and Urdea (1998) "Quantification of HCV RNA in clinical specimens by branched DNA (bDNA) technology" Methods in Molecular Medicine: Hepatitis C 19:71-78. In addition, reagents for performing basic bDNA assays (e.g., QuantiGene™ kits, amplification multimers, alkaline phosphatase labeled label probes, chemilumigenic substrate, capture probes immobilized on a solid support, and the like) are commercially available, e.g., from Panomics, Inc. (on the world wide web at www.panomics.com), and can be adapted for the practice of the present invention. Software for designing probe sets for a given mRNA target (i.e., for designing the regions of the capture extenders, label extenders, and optional blocking probes that are complementary to the target) is also commercially available (e.g., ProbeDesigner™ from Panomics, Inc.); see also Bushnell et al. (1999) "ProbeDesigner: for the design of probe sets for branched DNA (bDNA) signal amplification assays Bioinformatics 15:348-55.

Offset Probe Assay

Variations on the bDNA assay can be used to detect fragmentation in a target nucleic acid sequence. Fragmentation of the target nucleic acid can be detected as a loss or reduced signal when a break exists in the nucleic acid sequence between separated target complimentary sequence sites for label extenders and capture extenders (which are bound to a solid support through capture probes). Such a break between the CEs and LEs can break the link between the labels and the solid support so that label signals can be washed away in processing of the solid support. The sensitivity and/or useful detection range of the assay can be improved by comparison of the signal from an offset assay to a control assay wherein both CEs and LEs exist on both sides of the target nucleic acid break. A resulting ratio of offset to control signals can be more indicative of fragmentation than absolute values, especially where target nucleic acid quantities are unknown.

Figure 18A:
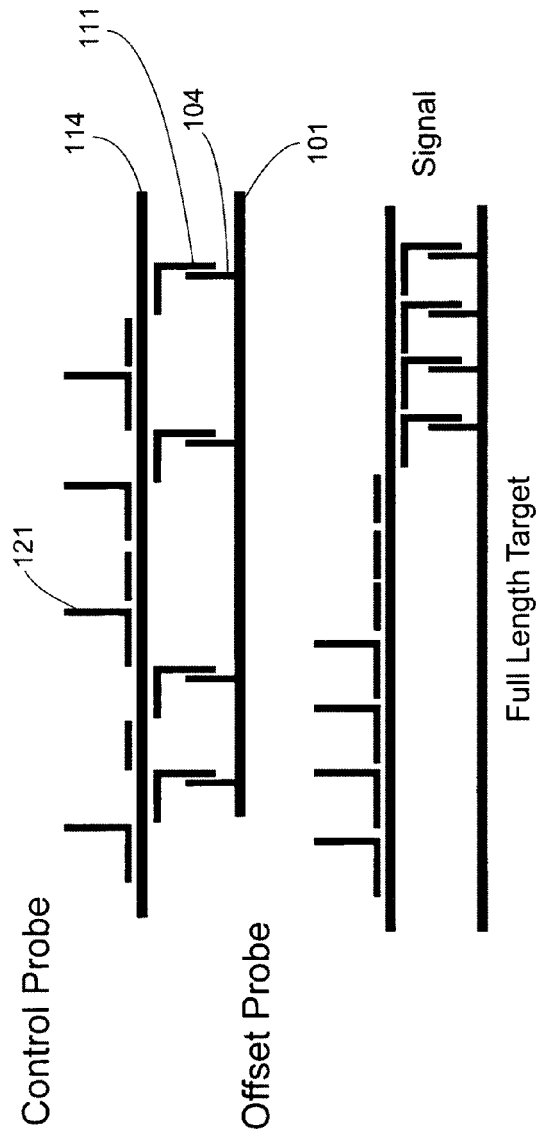
FIGS. 18A and 18B show schematic diagrams of offset probe and control schemes for detecting target nucleic acid fragmentation. Target RNA in FIG. 18A is unfragmented and thus a signal can be generated from label extenders retained at the solid support using either the control probe system or the offset probe system. Target RNA in FIG. 18B is fragmented between CE anchoring points and LE complimentary sites for the offset probe system, so a signal would not be generated by the bDNA assay. Meanwhile, for the same fragmented target RNA sequence in the control system, CE anchoring points and LE complimentary sites exist on both sides of the break, so a signal can still be generated for a bDNA assay using the control probe system.
Figure 18B:
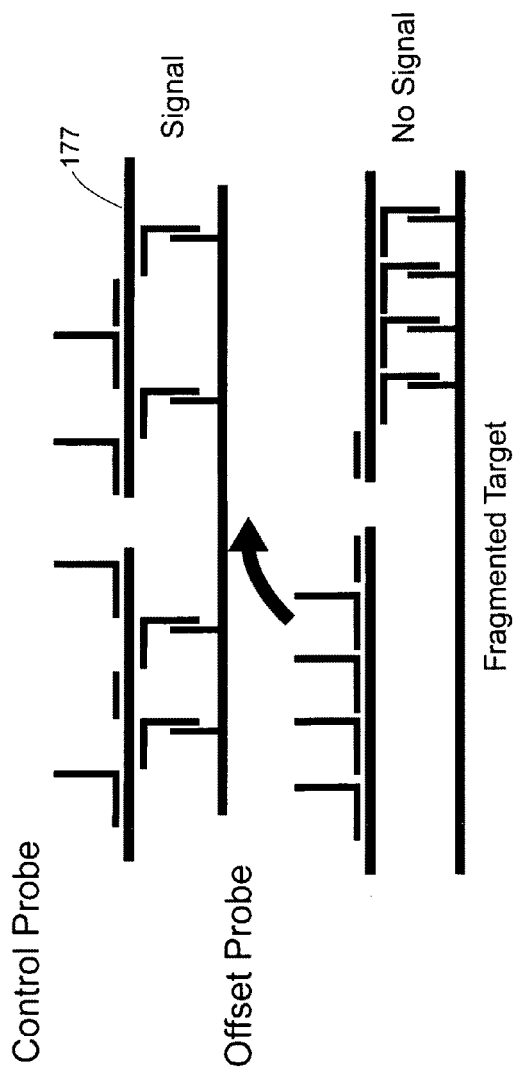

In an exemplary assay, as shown in FIGS. 18A and 18B, while the control probe set can provide a signal whether or not the target nucleic acid is fragmented, assay of the same fragmented target using the offset probe system can fail to generate a signal. As shown in FIG. 18A, a control probe system of interspersed LE 121 and CE 111 probes can effectively capture full length target nucleic acid 114, which is decorated with dispersed label extenders 121, thus allowing generation of a strong control signal. The full length target also allows a strong signal to be generated in the offset probe system by connecting offset label extenders to the solid support, through the capture extenders and capture probes 104. As can be seen in FIG. 18B, signal continues to be generated with the control probe set, even where the target nucleic acid sequence 177 in the test sample, is fragmented. The control probe set captures the target sequence (along with label extenders) on both sides of the break so that the ability to generate a signal is not lost, e.g., during process washes of the solid support. However, because the target nucleic acid is broken in the space between offset system LE target sequence sites and CE target sequence sites, no signal can be generated using the offset probe set of FIG. 18B. Although a fragment without bound LE probes is captured, the fragment with bound LE probes is not. Any signal associated with the bound offset LE probes will be lost when hybridization solution is washed off the solid support. It is envisioned that the positions of offset LEs and CEs can be established so that a break (or lack thereof) at a particular region or point along a target nucleic acid sequence can be detected.

In one embodiment, offset probes are designed so there is one CE target sequence site at or near one end of the target nucleic and one or more LE target sequence sites at the other end of the target nucleic acid. In preferred embodiments, the LE and CE sites are not immediately adjacent, but separated by a section of nucleic acid not complimentary to any LE or CE probe. A break anywhere between the CE complimentary target sites and LE target sites would result in no signal generation represented for that fragmented target by the offset system. The higher the proportion of target nucleic acids in a sample with such a break, the weaker the signal that could be generated, thus enabling a quantitative standard curve to be prepared using such a system. In a preferred embodiment, LE sites are present only near the two ends of the target nucleic acid, while one or more CE sites are present only between the two ends, e.g., near the center of the target nucleic acid, e.g., separated by a sequence not complimentary to any LEs or CEs of the system. In such a case, a break between the CE sites and one end would reduce the ability to generate a signal by, e.g., half; while breaks between the CE sites and each end would eliminate the ability of the system to generate a signal altogether.

In preferred embodiments of the offset probe system, LE target sequence sites are designed for sensitivity to breakage between the site and the nearest 3' and/or 5'CE target sequence site on the target nucleic acid. For example, in many cases for this technology it is preferred that there be no CE site between the LE site and one end of the target nucleic acid, so that if there is a break between the LE site and one or more CE sites toward the other end, the LE will be lost (unassociated with a solid support) along with its signal potential. It is preferred that a substantial portion of the target nucleic acid exist between the LE target sequences and CE target sequences. For example, in preferred embodiments, not less than 10% of the nucleic acid sequence of the test nucleic acid lies between the two closest LE and CE sites along the nucleic acid. It is more preferred that more than 25%, more 50%, more than 75%, more than 90%, or more of the nucleic acid being tested for fragmentation be between the members of the closest CE/LE pair of sites. It is preferred that one or more offset label extender L1 sequences in the offset probe system are complimentary to sequences of the nucleic acid spaced at least one nucleotide base either 5' or 3' from all the C3 complimentary sequences; more preferably 5 or more, 10 or more, 25 or more, 50 or more, 100 or more 500 or more bases are between the L1 and C3 complimentary sequences of the test nucleic acid.

In other embodiments of the offset probe scheme, there can be some CE targets interspersed among LE targets on the target nucleic acid, and/or visa versa. For example, an offset probe system can be designed wherein the target nucleic acid is captured near the two ends while the LE target sequence sites are spaced away from the CE sites, e.g., near the center of the target nucleic acid. In such a case, the ability to generate a signal would not be lost by a single break of the nucleic acid but could be lost with a break on each side of the LE target sites. It is envisioned that additional variant configurations of CE/LE spacing and dispersion would gradually or ultimately result in the loss of an ability to generate a signal with enough breaks between CE and LE sites. However, in other preferred embodiments, not more than 25% of the LE target sites are between two or more CE target sites; or not more than 25% of the CE sites are between two or more of the LE sites. In more preferred embodiments, not more than 10% of the LE target sites are between two or more CE target sites; or not more than 10% of the CE sites are between two or more of the LE sites. In more preferred embodiments, not more than 5% of the LE target sites are between two or more CE target sites; or not more than 5% of the CE sites are between two or more of the LE sites. In most preferred embodiments, CE and LE target sequence sites are not interspersed along the target nucleic acid sequence, i.e., no LE target sites are between any two CE target sites and/or no CE sites are between any two LE sites.

To normalize the offset probe assay results and to aid in interassay comparisons, it can be useful to provide fragmentation assay results in the form of a ratio of test assay results to control assay results. The control assay, e.g., using multiple interspersed LE/CE probe target sites, can be carried out on a different nucleic acid, the test nucleic acid full length, and/or with the test nucleic acid from the same sample being analyzed. In preferred embodiments the same test sample is analyzed by both the control assay and offset assay to provide the ratio. Particular ratios can be correlated to certain degrees of fragmentation. For example, a standard curve of ratios versus degree of fragmentation can be provided so that a ratio for a particular sample can be correlated to the level of fragmentation in that sample. Such information can be useful, e.g., in a choice of degraded IVT RNA standard to use in quantitation of an mRNA in the sample.

EXAMPLES

The following examples are offered to illustrate, but not to limit the claimed invention.

Example 1

Comparison of Post-Homogenization Separation to Pre-Homogenization Extraction of FFPE Tissue Slide Hydrophobic Components To demonstrate equivalence and improvements of post-homogenization separation over pre-homogenization organic extraction, FFPE sample mRNAs were compared using the branched DNA technology with and without pre-solubilization dewaxing. Samples from >10 yr-old matched human lung normal and tumor FFPE samples were pooled as three 10 micron sections. For one pair of samples ("0"), homogenates were prepared with wax separation after solubilization. For a second pair of samples ("1"), homogenates were prepared with 1× dewaxing organic extraction step before solubilization. For a third pair of samples ("2"), homogenates were prepared with 2× dewaxing organic extraction cycles. Extracts were tested using ribosomal protein S3 (RPS3, NM_001005 housekeeper or Reference control RNA) and Lactate dehydrogenase A (LDHA, NM_005566; 2-3× induction in tumor samples) as described by Yang et al. 2006. Modified probe design software was developed to design oligonucleotide probe sets for target genes in branch DNA assays (Bushnell et al., 1999). A probe set for a target gene consists of three types of oligonucleotide probes (CE—capture extender, LE—label extender, and BL—blocking probe) covering a contiguous region of the target, which allows the capture of target RNA to the surface of plate well and hybridization with branched DNA signal amplification molecule. For each target sequence, the software algorithm identified regions that can serve as annealing templates for CEs (5-10 per gene), LEs (10-20 per gene), or BLs to substantially fill the remaining space. The branched DNA assays were performed according to the procedure of QuantiGene® Reagent System (Panomics), which was previously described in detail (Wang et al., 1997, Kern et al., 1996). Briefly, 10 µL tissue homogenate was mixed with 40 µL Lysis Mixture (Panomics), 40 µL Capture Buffer (Panomics), and 10 µL target gene-specific probe set (CE, 1.65 fmol/µL; LE, 6.6 fmol/µL; BL, 3.3 fmol/µL). Each sample mixture is then dispensed into an individual well of a Capture Plate (Panomics).

As can be seen in the graphs of FIG. 3, the determination of mRNA expression levels determined with post-solubilization separation is comparable, if not improved, as compared to the 1× and 2× phase extraction procedures.

Example 2

Equivalent Spike Recovery from FFPE Samples

An additional experiment was performed demonstrating that the recovery of RNA from FFPE sections is equivalent for post-solubilization separation and pre-solubilization extraction. Methods were as described above for the Lactate dehydrogenase A (LDHA, NM_005566) and ribosomal protein S3 (RPS3, NM_001005), except a known amount of in vitro transcribed (IVT) RNA from the bacterial gene dihydrodipicolinate reductase (dapB, L38424 not expressed in the human lung tissue) was added to a solublized FFPE sample. The data show yields were comparable between the 2× dewax extraction technique and physical wax separation technique. Using either procedure, the capture efficiency (spike recovery) of the spiked-in dapB IVT RNA ranged from 90-110%.

Example 3

Use of Repetitive Ribosomal DNA to Determine Efficiency of FFPE Tissue Solubilization and Number of Cells in the FFPE Sample An investigation was made to determine if accurate estimates of cell numbers can be made based on repetitive DNAs. In particular, cell counts for tumor and other aneuploid cells were determined using standard curves based on quantitation of ribosomal DNA genes.

Ten (10) cell lines were chosen with an average of about ten (10) ribosomal gene clusters per diploid genome. Four thousand (4000) cells of each cell line were lysed in QuantiGene Lysis Buffer (Panomics) and 10 cell line lysates were pooled; i.e. 10 cell lines in total or 40,000 cells are in a total volume of 110 ul.

Figure 6:
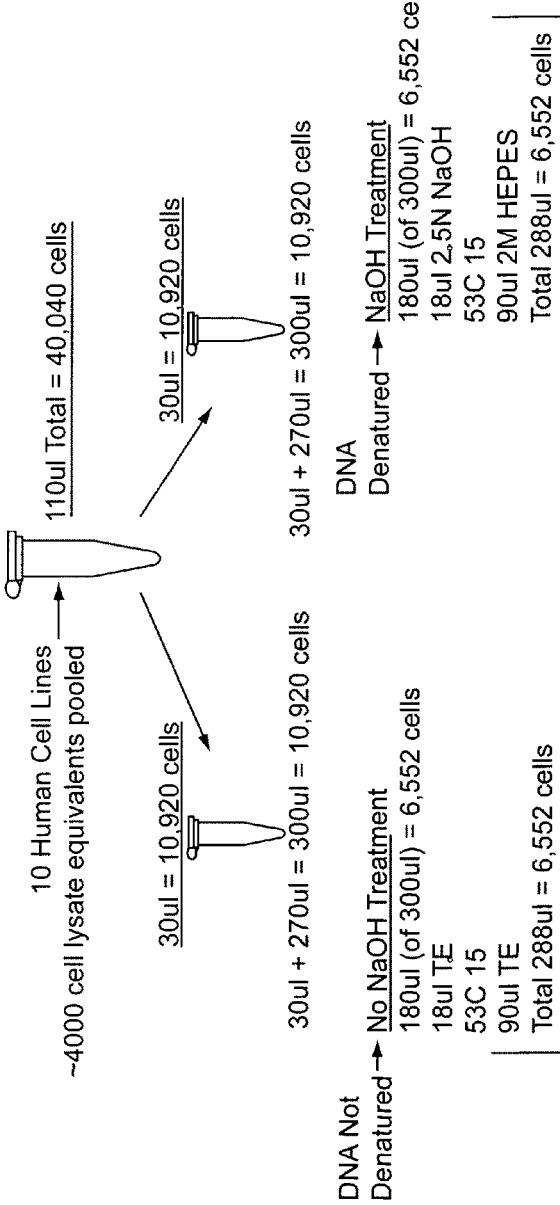
FIG. 6 shows a schematic flow diagram of a protocol to establish a cell number standard curve based on rDNAs.
Figure 7:
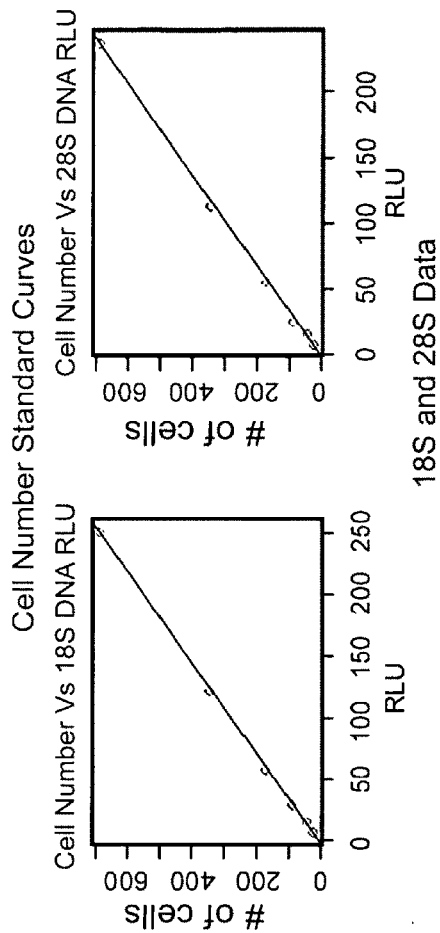
FIG. 7 shows standard curves of cell numbers versus bDNA assay output for 18S and 28S ribosomal DNAs.

Thirty microliters (30 ul) each were transferred to separate microfuge tubes, one to denature the DNA to measure the ribosomal DNAs (18S & 28S rDNA) and another undenatured control to measure background of the assay. Next, each tube was diluted to 300 ul total by adding 270 ul TE buffer. 180 ul each of denature and control samples were transferred to reaction tubes. 18 ul of 2.5N NaOH was added to the tube containing the DNA for denaturing and 18 ul TE was added to the control aliquot before heating the tubes at 53° C. for 15 minutes (see FIG. 6). After the heating step, 90 ul of 2M HEPES was added to both control (undenatured) and denatured samples. The DNA in the control sample remained double stranded, whereas the denatured DNA sample was substantially in the single-stranded form. Cell number standard curves were established by adding denatured samples (30 ul, 15 ul, 7.5 ul, 3.8 ul, 1.9 ul, 0.95 ul or 683, 341, 171, 85, 43, 21 cell equivalents, respectively) to QuantiGene assays (see FIG. 7). Instead of using typical antisense probe sets to measure mRNA, sense probe sets are used to quantify the amount of 18S and 28S ribosomal DNA in the samples.

Because the 18S and 28S ribosomal probe sets gave virtually the same results for the pool of cell lines, the amount of ribosomal DNAs in FFPE tumor samples and FFPE cell line controls was determined using only the 18S ribosomal probe sets. FFPE Tumor and cell line control sections were solublized and tested as described above. Briefly, sections were solublized in 300 ul QuantiGene Homogenization Buffer and 2 ul diluted $10^3$. 60 ul of $10^3$ diluted sample was transferred to a microfuge tube and denatured by adding 6 ul of 2.5N NaOH followed by heating to 53° C. for 15 minutes. At the end of denaturation the solution was neutralized by adding 30 ul of 2M HEPES with a vortex mix. 30 ul of the denatured solution was added to the QuantiGene assay and 18S ribosomal DNA was quantified using the 18S rDNA cell number standard curve (pooled 10 cell lines) as described above.

Figure 8:
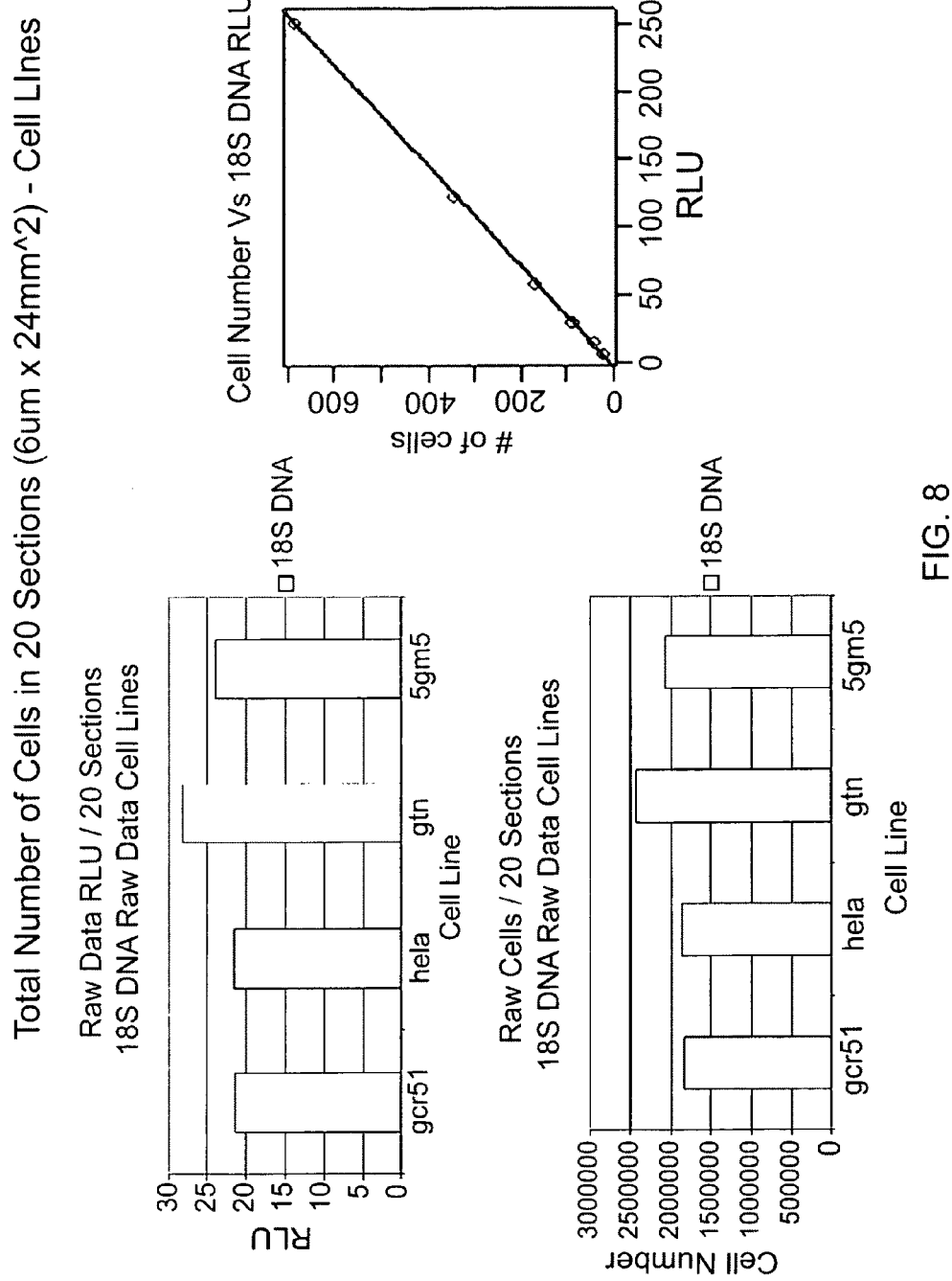
FIG. 8 shows a standard curve of cell number versus 18S DNA. Histograms show the 18S DNA standard curves can provide substantially accurate cell number determinations, even for aneuploid cell lines.

A known number of cells from four cell lines were fixed with formalin and embedded in paraffin. Twenty sections (6 um×20 mm² = ~100,000 cells/section = total ~2×$10^6$ cells) of each cell line were solublized in 600 ul QuantiGene Homogenization Buffer, DNA denatured, and quantified using the 18S rDNA probe sets as described in above. Using the 18S rDNA cell number standard curve, cell counts between 2-2.5×$10^6$ were determined for the cell line FFPE samples each with 20 sections. See FIG. 8.

Example 4

Cell Number Quantitation from FFPE Tumor Tissue Sections

Figure 9:
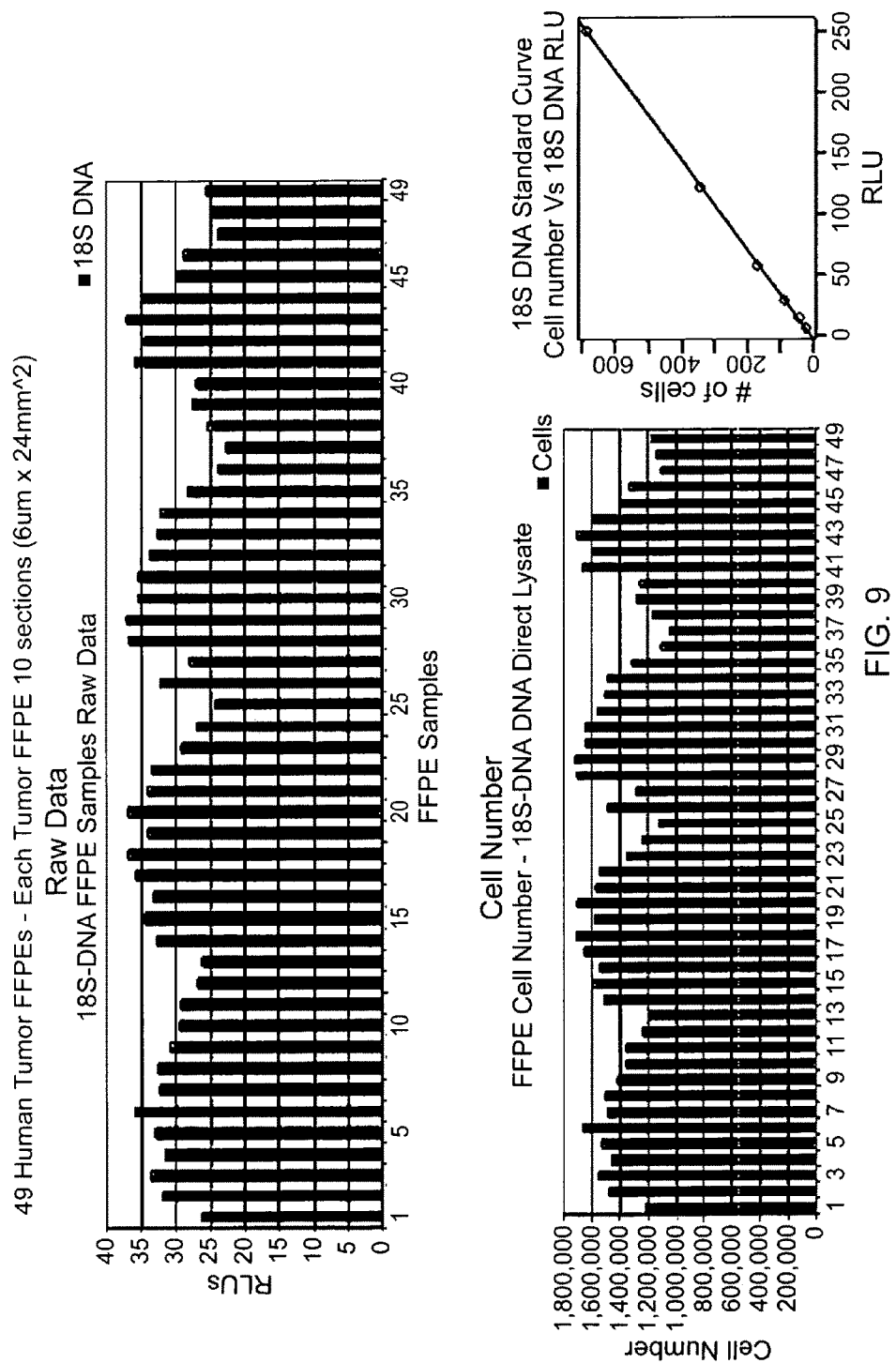
FIG. 9 shows quantitation of cell numbers obtained by bDNA assay of 18S DNA for 49 tumor tissue scrapings from FFPE slides.

Ten sections (6 um×24 mm²; all sections>85% tumor) each from 49 tumors (24 lung, 25 colon) were solublized in 300 ul QuantiGene Homogenization Buffer, DNA denatured, and quantified using the 18S rDNA probe sets as described in above. Using the 18S rDNA cell number standard curve, between 1.2-1.7×10$^6$ cells/FFPE tumor sample were quantified for 10 sections total. See FIG. 9.

Example 5

Quantifying RNA Molecules Using Intact and Degraded IVT RNA Standard Curves

In Vitro Transcribed RNAs (IVTs) using cloned genes can be used as standard curves to calculate the number of RNA molecules. FFPE mRNAs are typically somewhat degraded, e.g., by fragmentation processes. We have found that degraded IVT standard analysis curves can be compared to curves for undegraded full length RNAs to determine an assay efficiency for analysis of a degraded sample. For example, the QuantiGene assay can be used to accurately quantify degraded mRNA from clinical samples.

Figure 10:
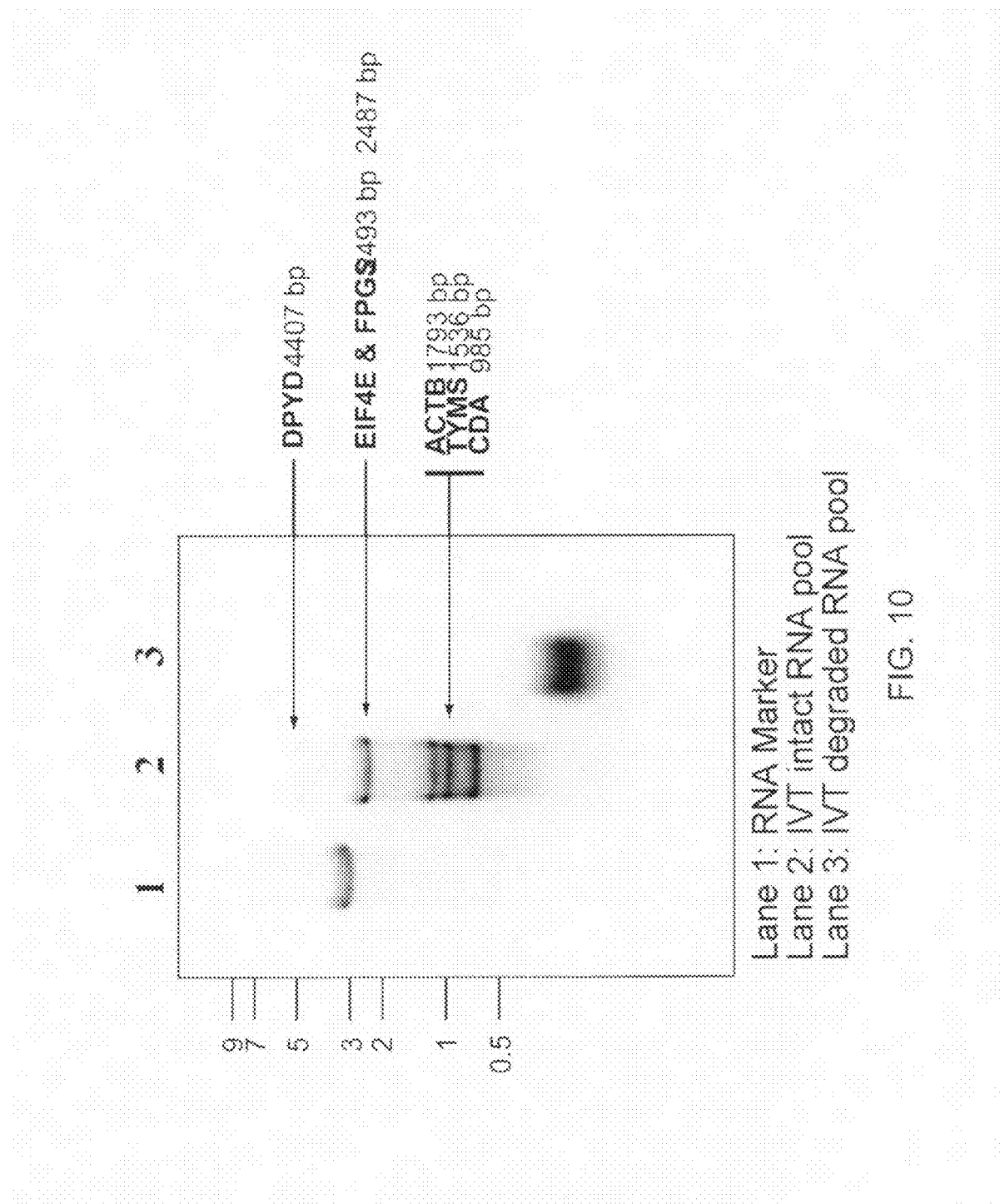
FIG. 10 shows gel electrophoresis of intact full length in vitro transcribed (IVT) RNAs and hydroxide degraded IVT RNAs.

IVTs were synthesized according to Ambion instructions. A portion of the intact RNAs were degraded to 100-300 bp to mimic the size of FFPE RNAs. To accomplish the desired size of degraded RNAs, undegraded full length IVT RNAs are degraded in 0.1N NaOH for 9 minutes. The reaction was neutralized using an equivolume of 0.1N HCl to stop the degradation process. The gel shown in FIG. 10 shows seven undegraded full length in vitro transcribed RNAs (pooled in lane 2) and the same seven IVT RNAs degraded and pooled for the gel electrophoresis.

Figure 11:
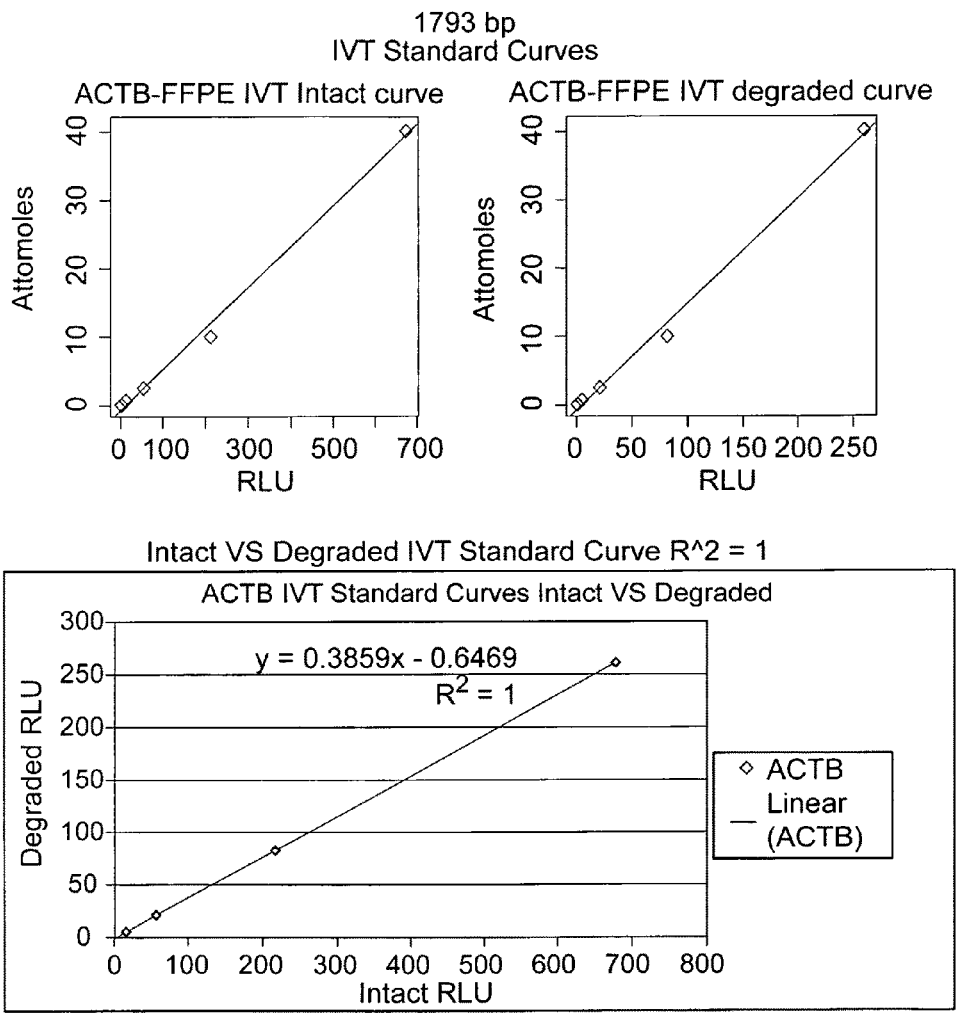
FIG. 11 shows standard curves for RNA attamole input to a bDNA assay verses assay signal output for full length or degraded IVT transcribed RNA standards. A standard equation is presented for the relationship between assay output for intact versus degraded RNA.
Figure 12:
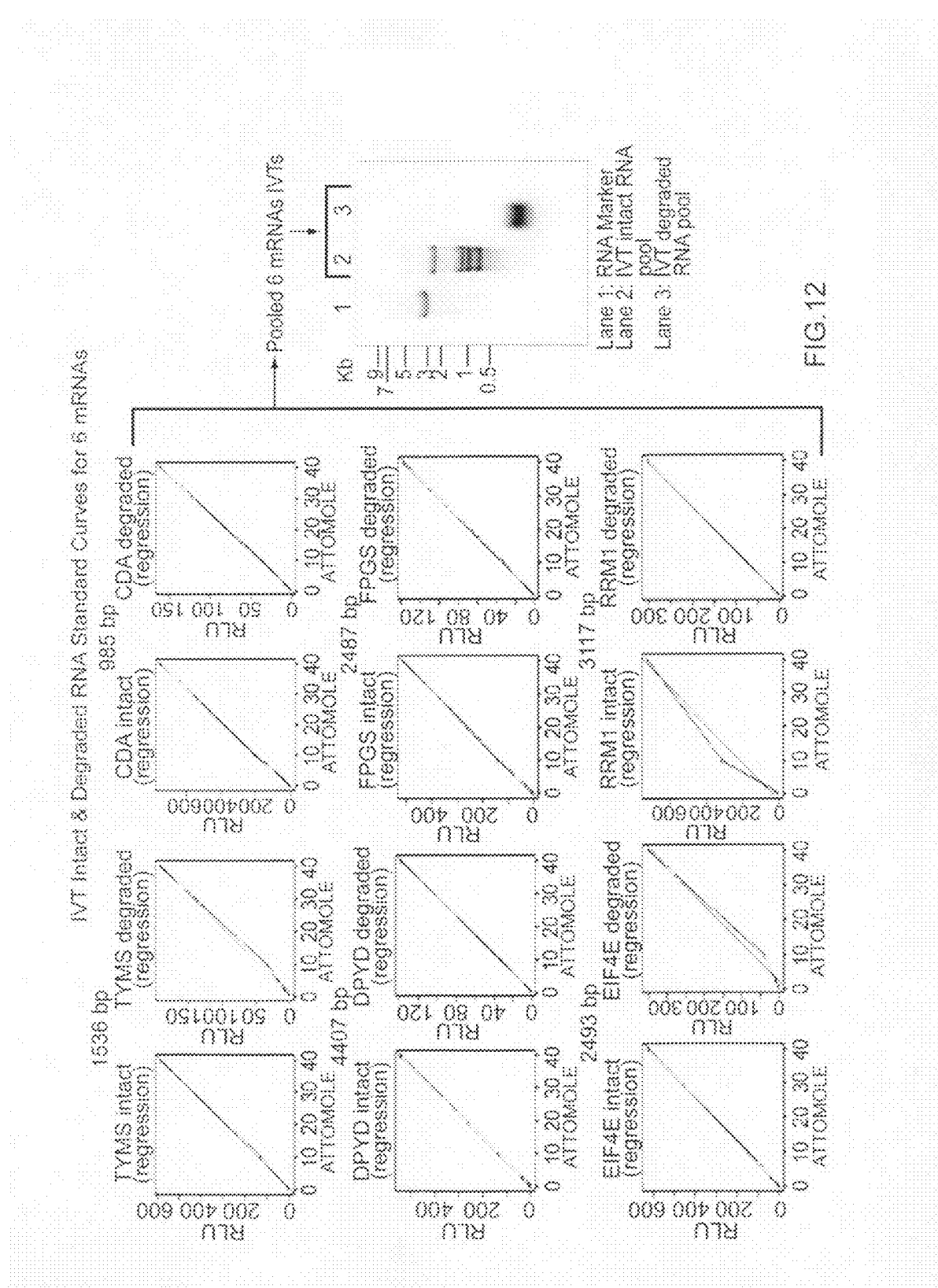
FIG. 12 shows intact and degraded IVT RNA standard curves for 6 mRNAs.

Next the IVT concentration was determined and the solutions serially diluted to 40, 10, 2.5, 0.625, 0.156, and 0.039 attamole ($^{-18}$ mol). As shown in FIG. 11, for example, beta-Actin (ACTB) IVT undegraded full length RNA (1739 bp) and corresponding IVT degraded RNA (see gel FIG. 10) were quantified using beta-Actin specific probe sets (Panomics) and standard curves established. When the standard curves are compared to each other, a R2 value of 1 is determined (R-squared refers to the fraction of variance). As can be seen, the sensitivity of the ACTB specific probe sets using degraded ACTB IVT (100-300 bp) is ~40% (slope 38.6%) of the undegraded ACTB IVT (1739 bp) for all concentrations. Similar findings were found for the other 6 genes using both undegraded full length (ranging in size from 985 bp to 4407 bp) and degraded IVTs (see FIG. 12).

Figure 13:
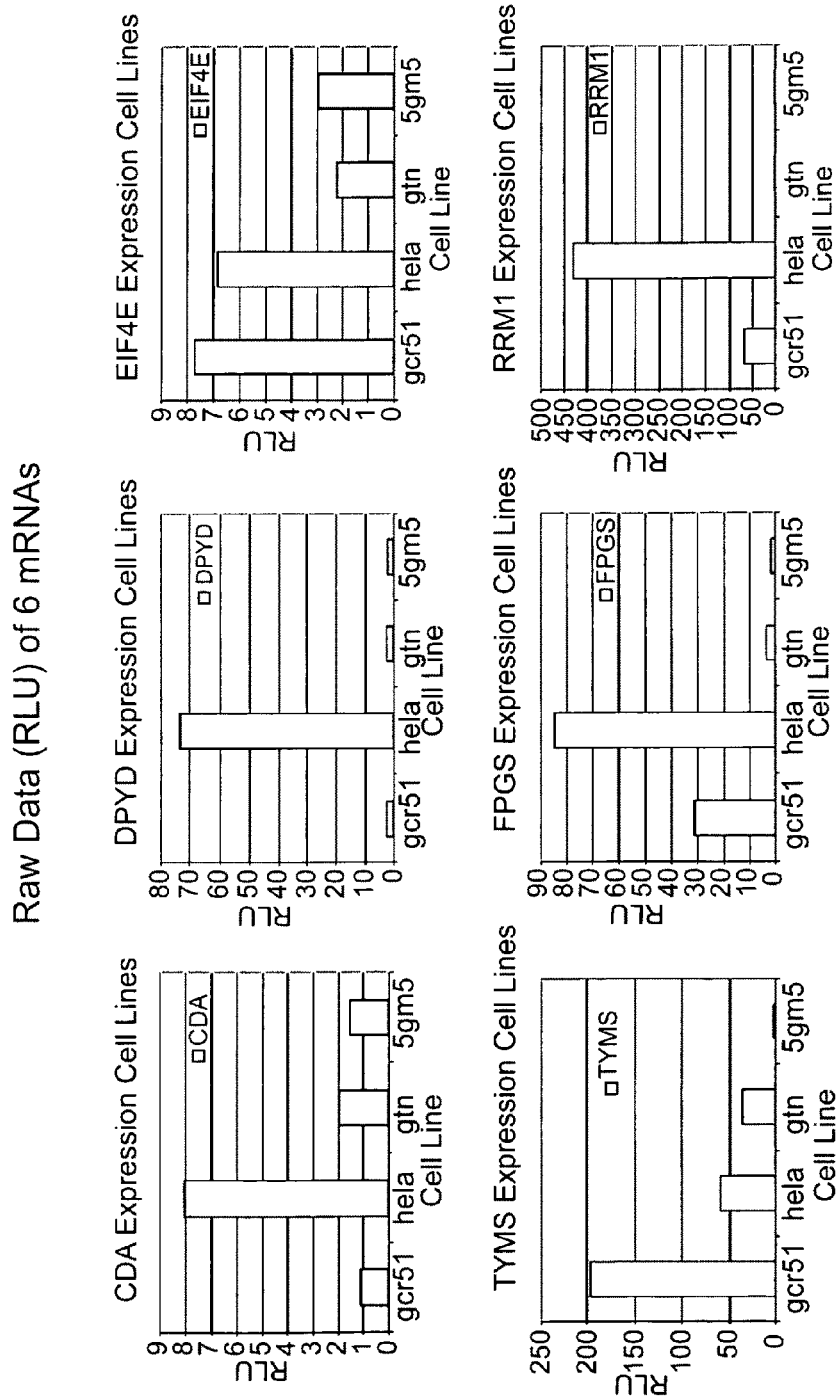
FIG. 13 shows raw assay output data reflecting expression of 6 mRNAs in 4 formalin fixed, paraffin embedded, cell lines.
Figure 14:
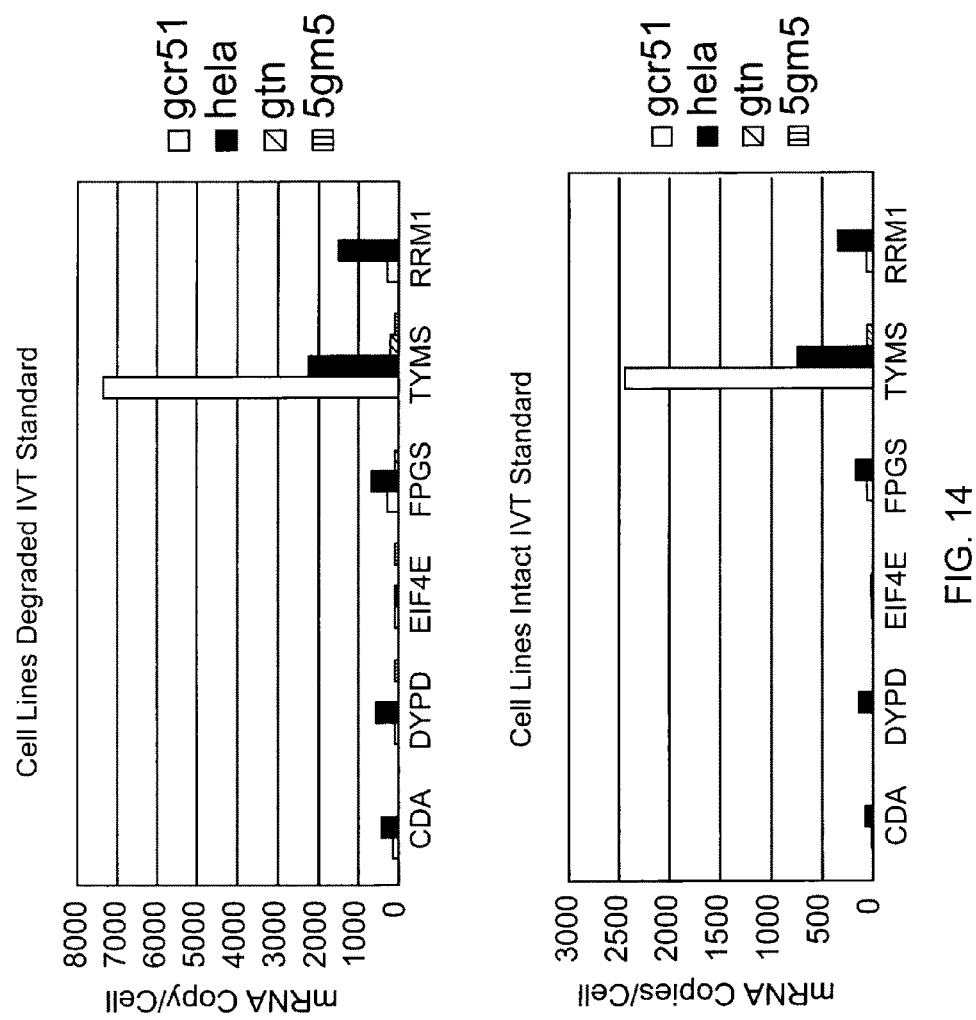
FIG. 14 shows copy numbers per cell for 6 mRNAs calculated based on intact or degraded IVT RNA standard curves.

Known numbers of cells for 4 cell lines (previously discussed at the end of Example 3) were fixed with formalin and embedded in paraffin (twenty sections, 6 um×20 mm$^2$=~100,000 cells/section=total ~2×10$^6$ cells) and solublized in 600 ul QuantiGene Homogenization Buffer were used to quantify the amount using equivolumes of input samples for all 6 mRNAs in all 4 cell lines. First, bDNA assays were used to determine relative amounts of expression in each cell line for each of 6 mRNAs (see FIG. 13). Then, from the raw data, the attomoles of each of the 6 mRNAs was calculated using both IVT standard curves (undegraded & degraded, see above). Finally, the attomoles were divided by the cell number of each cell line using the 18S rDNA/cell number standard curve to determine copy number per cell for each mRNA and cell line (see FIG. 14). The copy number calculated from the degraded IVT standard curves correlated closely with the copy numbers calculated for the fresh full length IVT RNA samples using the undegraded IVT standard curve. Thus, the degraded IVTs better represent mRNAs derived from homogenized FFPE samples, and provide better standard materials for quantitation of such mRNAs.

Figure 15:
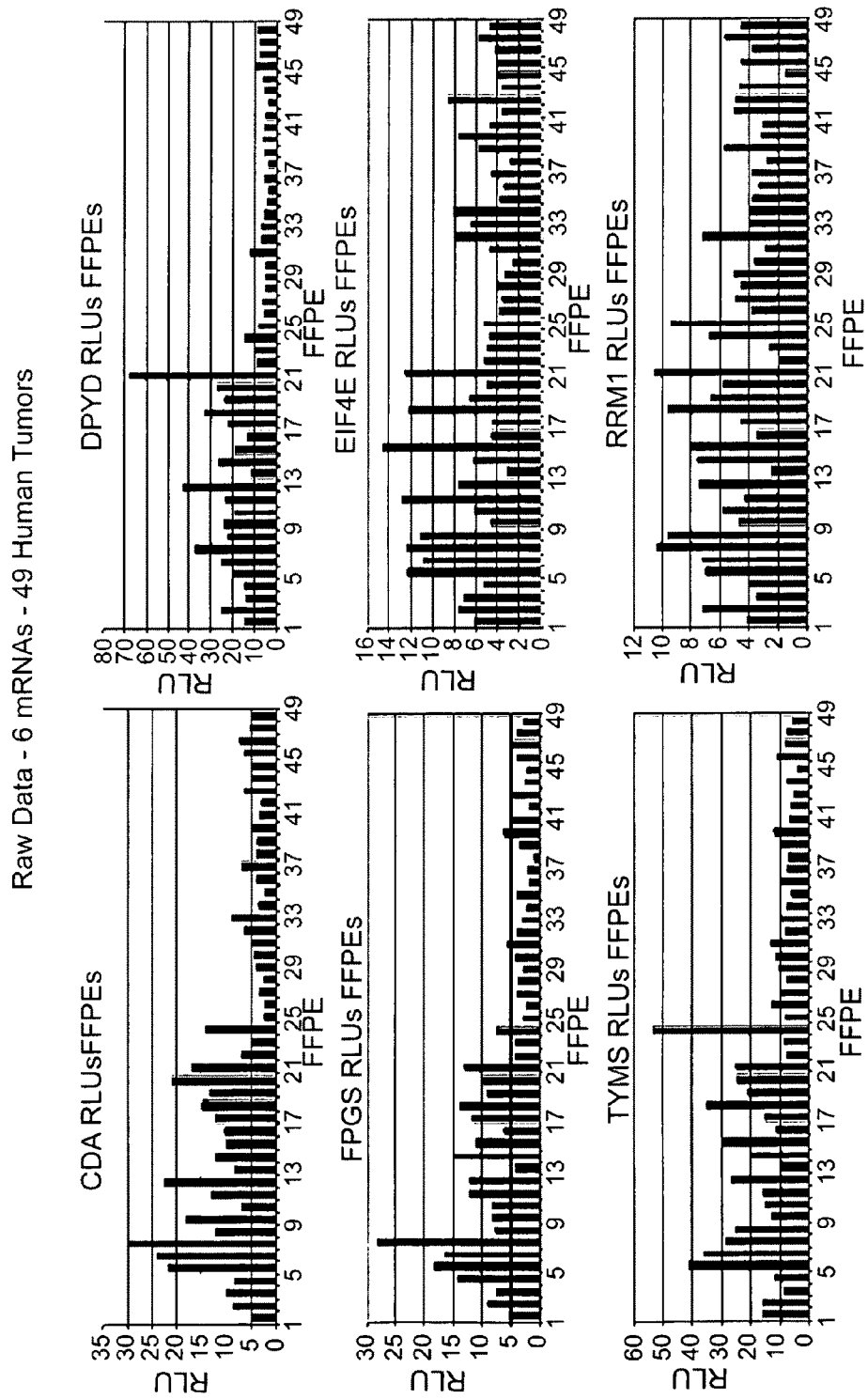
FIG. 15 shows raw bDNA assay output data for 6 mRNAs determined in 49 human tumors.

In an additional example of mRNA quantitation and copy number determination, the ten sections (6 um×24 mm$^2$; all sections>85% tumor) each from 49 tumors (25 lung, 24 colon) were solublized in 300 ul QuantiGene Homogenization Buffer as described above for the 18S and 28S rDNAs. The resultant homogenates were used to quantitate the amount of the 6 mRNAs using the QuantiGene specific probe sets (see above). IVT standard curves were the same used to measure the mRNAs in the 4 cell lines. FIG. 15 shows the raw relative quantitative data for each of the mRNAs in all 49 tumors.

Figure 16:
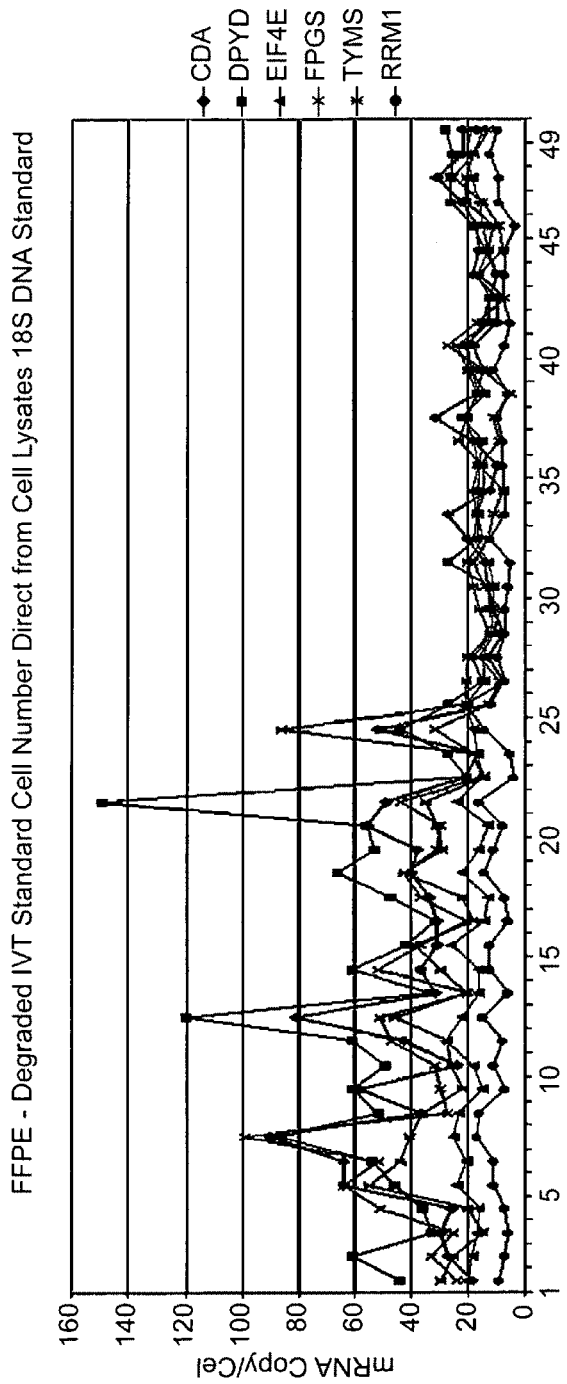
FIG. 16 shows a chart displaying the determined mRNA copy number per cell, based on degraded IVT RNA standards, for 6 mRNAs in 49 tumor cell samples.

The attomoles of each mRNA in all tumors was calculated from the degraded IVT standard curve and divided by the number of cells in each of the tumor samples (total of 10 sections) for use in calculating the mRNA copies per cell. This data is shown in FIG. 16. It was noted that a clear trend exists with the copy number per cell for expression levels (mRNAs) in some of the genes being elevated in the lung tumors (1-25) and not in the colon tumors (26-49).

Example 6

Determination of Sample RNA Degradation

Fragment length of an RNA was assessed for a tissue block. This assessment can aid in, e.g., selection of FFPE blocks with adequate RNA integrity and in choice of an IVT RNA assay standard for use with a sample. After FFPE solubilization, a sample was tested using two probe sets for an mRNA (gene) of interest. Either standard dispersed control probe sets (see FIGS. 18A and 18B) or test probe sets with off-set CE and LE sites were are added to the tissue homogenizing buffer for over night hybridization. The control and test samples were processed the next day according to standard bDNA assay procedures.

Figure 19:
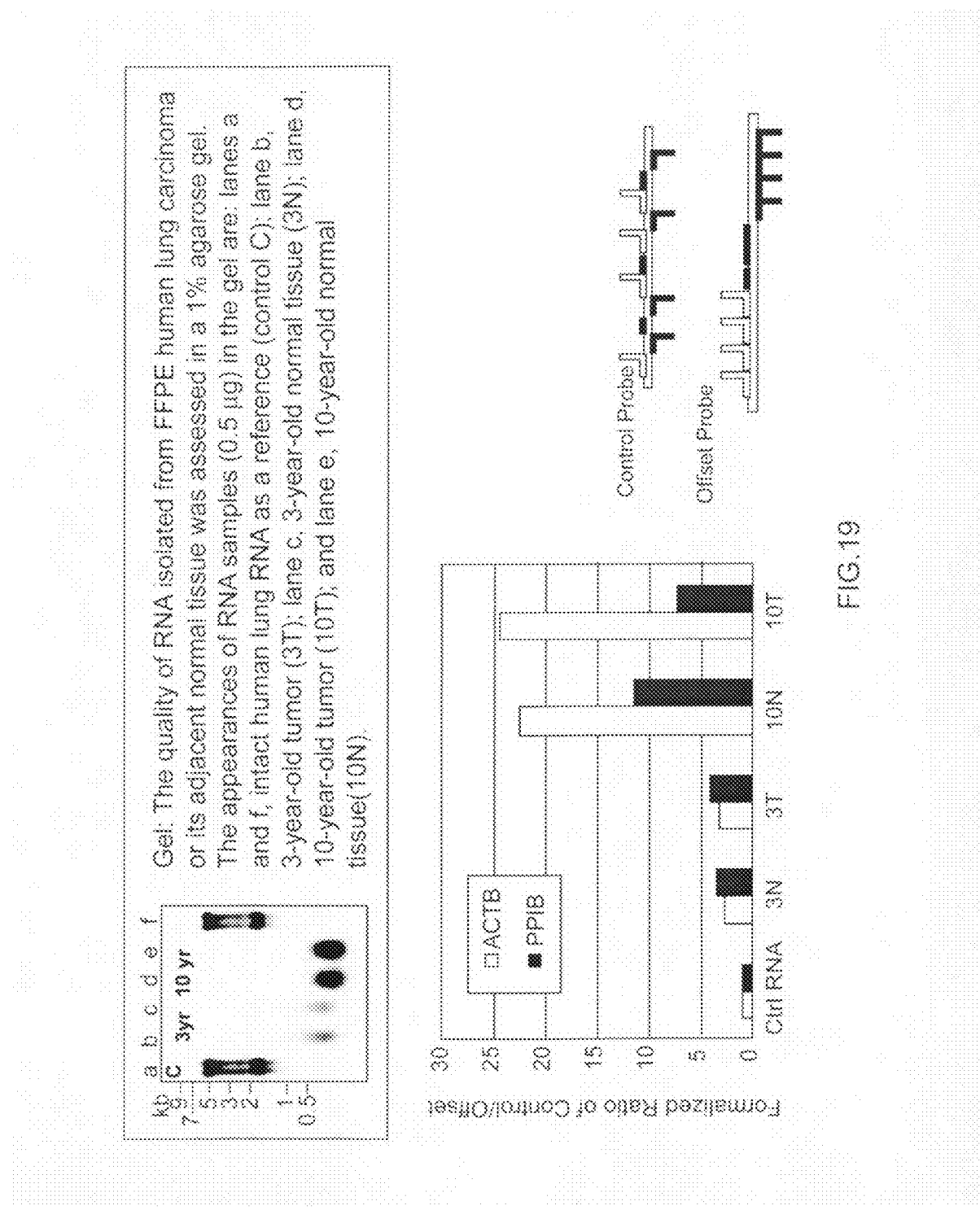
FIG. 19 shows how the ratio of control to offset probe signals can be correlated to RNA degradation, as visualized on an agarose gel.

As can be seen in FIG. 19, FFPE samples of varying RNA quality were tested. First the quality of purified RNA is evaluated by gel electrophoresis. The RNA in 3 year old samples (both tumor and normal RNA) presented less fragmentation than those of the year old samples. Next, intact control RNA and RNA from both 3 year old and 10 year old FFPE samples were subjected to bDNA analysis with either dispersed control probes or off-set fragmentation test probes. The quality of the RNA was assessed by determining the ratio of the assay signal for control over offset assay results. We found the ratio increases with increasing RNA degradation (control ratio=1; 3 year old=3-4; 10 year old=7-24). The offset bDNA probe scheme offers a simple approach to assess the quality of RNA from any sample.

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, many of the techniques and apparatus described above can be used in various combinations.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of collecting a nucleic acid from formalin fixed paraffin embedded cells, said method comprising:
   suspending the formalin fixed paraffin embedded cells in an aqueous solution;
   incubating the suspension 3 hours or more at a temperature ranging from 40° C. to 100° C., and at least 2° C. below the Tm for double stranded DNA of the cells, whereby the paraffin melts and the nucleic acid is released from the cells into the aqueous solution, wherein the suspended cells incubated in the suspension are other than dewaxed cells; and,
   physically separating the aqueous solution from the paraffin after said incubation, thereby collecting the nucleic acid from the cells;
   wherein the paraffin has a melting point 71° C. or less and greater than 40° C.

2. The method of claim 1, wherein said suspending comprises scraping the cells from a microscope slide, douncing or vortexing.

3. The method of claim 1, wherein the aqueous solution comprises constituents selected from the group consisting of: PEG (polyethylene glycol), SDS (sodium dodecyl sulfate), SSC (saline-sodium citrate) buffer, $NaHPO_4$, EDTA (ethylene diamine tetra-acetate), denatured salmon sperm DNA (deoxyriboneucleic acid), formamide, and SSPE (saline-sodium phosphate EDTA) buffer.

4. The method of claim 1, wherein the aqueous solution comprises constituents selected from the group consisting of: blocking probes, capture extenders, label extenders, preamplifiers, label probes, amplification probes, amplification multimers, a protease, a lipase, a surfactant, or nuclease inhibitor.

5. The method of claim 1, wherein the aqueous solution comprises more than 150 ug/ml of a proteinase.

6. The method of claim 5, wherein the protease comprises a proteinase K.

7. The method of claim 1, wherein the incubation temperature comprises a temperature ranging from 52° C. to less than 80° C.

8. The method of claim 1, wherein the incubation temperature comprises a temperature of 65° C.

9. The method of claim 1, wherein said incubating comprises holding the suspension at the incubation temperature for 12 hours or more.

10. The method of claim 1, wherein said non-denaturing conditions include pH conditions that do not exceed pH 8.5 or a temperature of 70° C.

11. The method of claim 1, wherein said separating comprises a technique selected from the group consisting of: centrifuging, decanting, aspirating, filtering, pipetting, and solidifying the hydrophobic component at a temperature below the melting point.

12. The method of claim 1, further comprising capturing the nucleic acid on a solid support.

13. The method of claim 1, further comprising quantitating the nucleic acid by detecting the nucleic acid and comparing the detected nucleic acid to a standard.

14. The method of claim 13, wherein said detecting comprises a technique selected from the group consisting of: bDNA analysis, northern blot analysis, Southern blot analysis, polymerase chain reaction, nucleic acid sequencing techniques, and agarose gel electrophoresis.

15. The method of claim 1, further comprising phenol extraction of the separated aqueous solution.

16. The method of claim 1, wherein the aqueous solution is not chemically extracted with an organic solvent.

17. The method of claim 1, wherein the incubation temperature is at least 2° C. above the melting point temperature of the hydrophobic component.

18. The method of claim 1, wherein the incubation temperature ranges from 45° C. to 95° C.

19. The method of claim 1, wherein the incubation temperature is at least 5° C., or 10° C. below a Tm of the cell DNA.

20. The method of claim 1, wherein the incubation temperature is less than a temperature that would denature a preponderance of the cell DNA.

* * * * *